United States Patent [19]

Miller et al.

[11] Patent Number: 5,665,541
[45] Date of Patent: Sep. 9, 1997

[54] FORMATION OF TRIPLE HELIX COMPLEXES FOR THE DETECTION OF DOUBLE STRANDED DNA SEQUENCES USING OLIGOMERS WHICH COMPRISE AN 8-MODIFIED PURINE BASE

[75] Inventors: Paul S. Miller; Purshotam Bhan, both of Baltimore, Md.

[73] Assignee: The Johns Hopkins University, Baltimore, Md.

[21] Appl. No.: 194,789

[22] Filed: Feb. 10, 1994

Related U.S. Application Data

[63] Continuation of Ser. No. 751,813, Aug. 30, 1991, abandoned, which is a continuation-in-part of Ser. No. 368,027, Jun. 19, 1989, abandoned, which is a continuation-in-part of Ser. No. 924,234, Oct. 28, 1986, abandoned.

[51] Int. Cl.$^6$ ............... C12Q 1/68; C07H 21/00; C07H 21/04
[52] U.S. Cl. ............... 435/6; 536/23.1; 536/24.3; 536/25.3
[58] Field of Search ............... 536/23.1, 24.3, 536/25.3; 435/6

[56] References Cited

PUBLICATIONS

Stryer, L. Biochemistry 72, 602 (1988).
Miller et al. Biochemistry 31:6788–6793 (1992).
Beal, P. A. et al. (1991, Mar.) Science, vol. 251, 1360–1363.
Cooney, M. et al. (1988), Science, vol. 251, 456–459.
Young et al. (Nov. 1991) P.N.A.S. 88:10023–10026.
Wood et al. Biochem. (1990) 29(30):7024–7032.
Wang et al. FEBS Lett. (1994) 355:11–14.
Jetter et al. (1993) BIOCHEM. 32:3249–3254.
Miller et al. BIOCHEM. (1993) 32 2999–3004.
Haner et al. BIOCHEM. (1990) 29(42):9761–9765.

*Primary Examiner*—Lisa B. Arthur
*Attorney, Agent, or Firm*—Lyon & Lyon

[57] ABSTRACT

A specific segment of double stranded DNA may be detected or recognized by formation of a triple helix structure using an Oligomer comprising an 8-modified purine base such as 8-oxo-adenine or 8-oxo-guanine to form a detectable triple helix complex. Function or expression of double stranded DNA segments may be prevented by triple helix formation. Novel Oligomers comprising an 8-modified purine base are useful in triple helix formation, and may be optionally derivatized with DNA modifying groups.

30 Claims, 12 Drawing Sheets

FIG_1a_
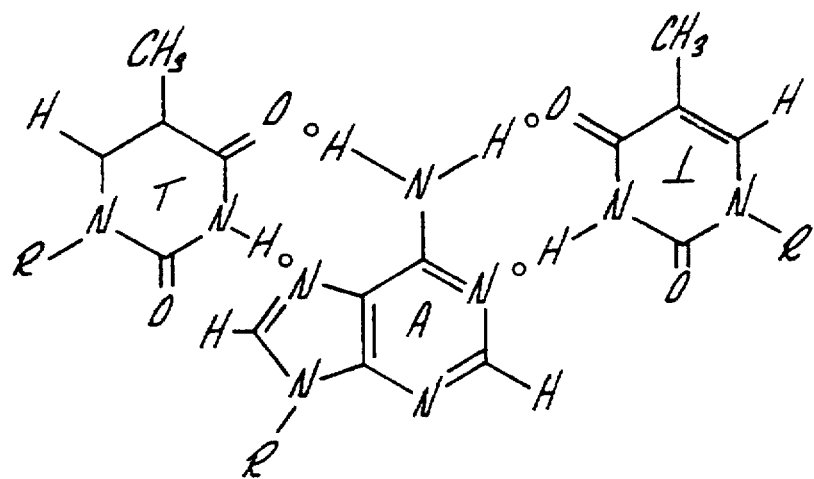
TA1
FIG_1b_
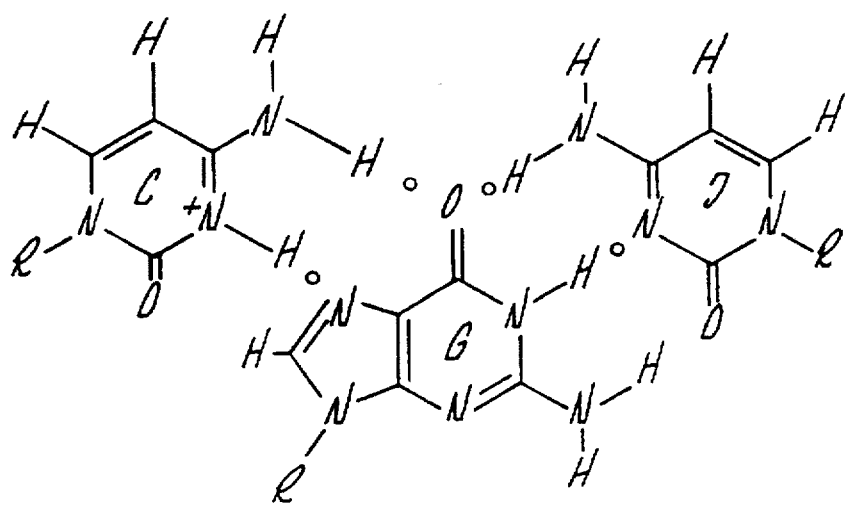
C⁺GJ

AAT

TAA

GGC

CGG

FIG. 5
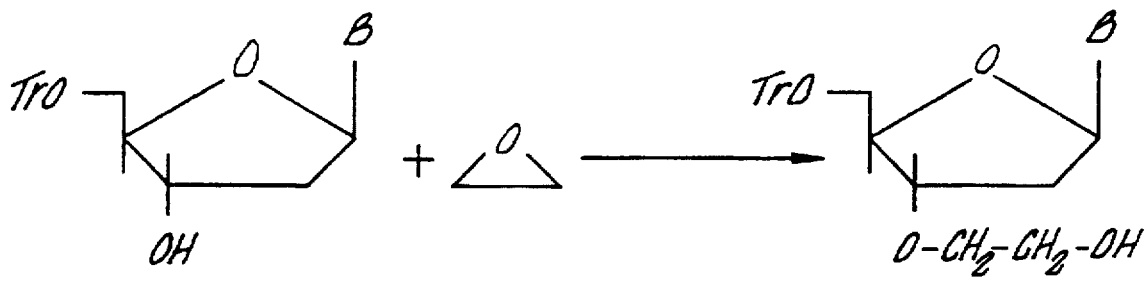
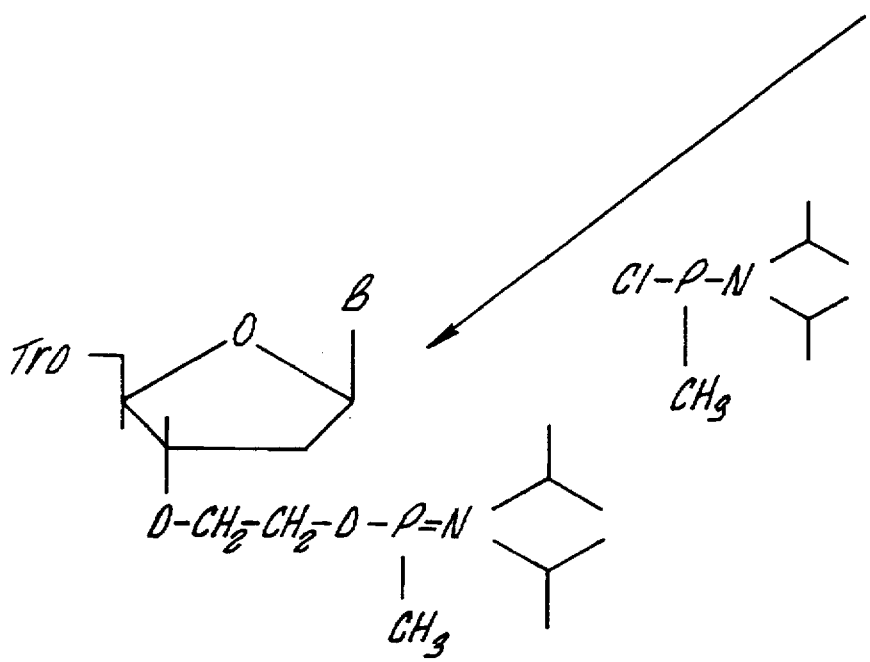
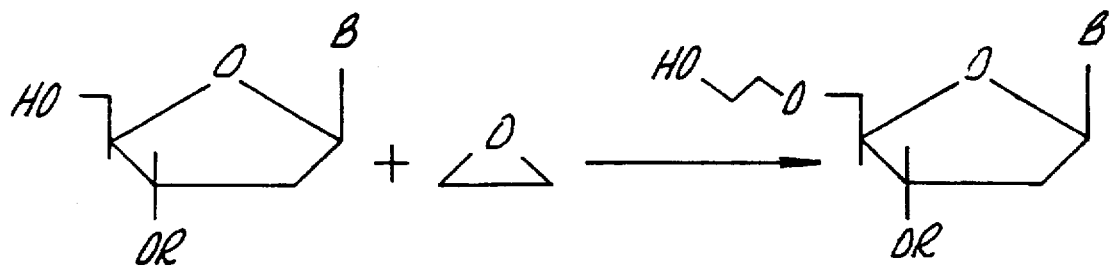

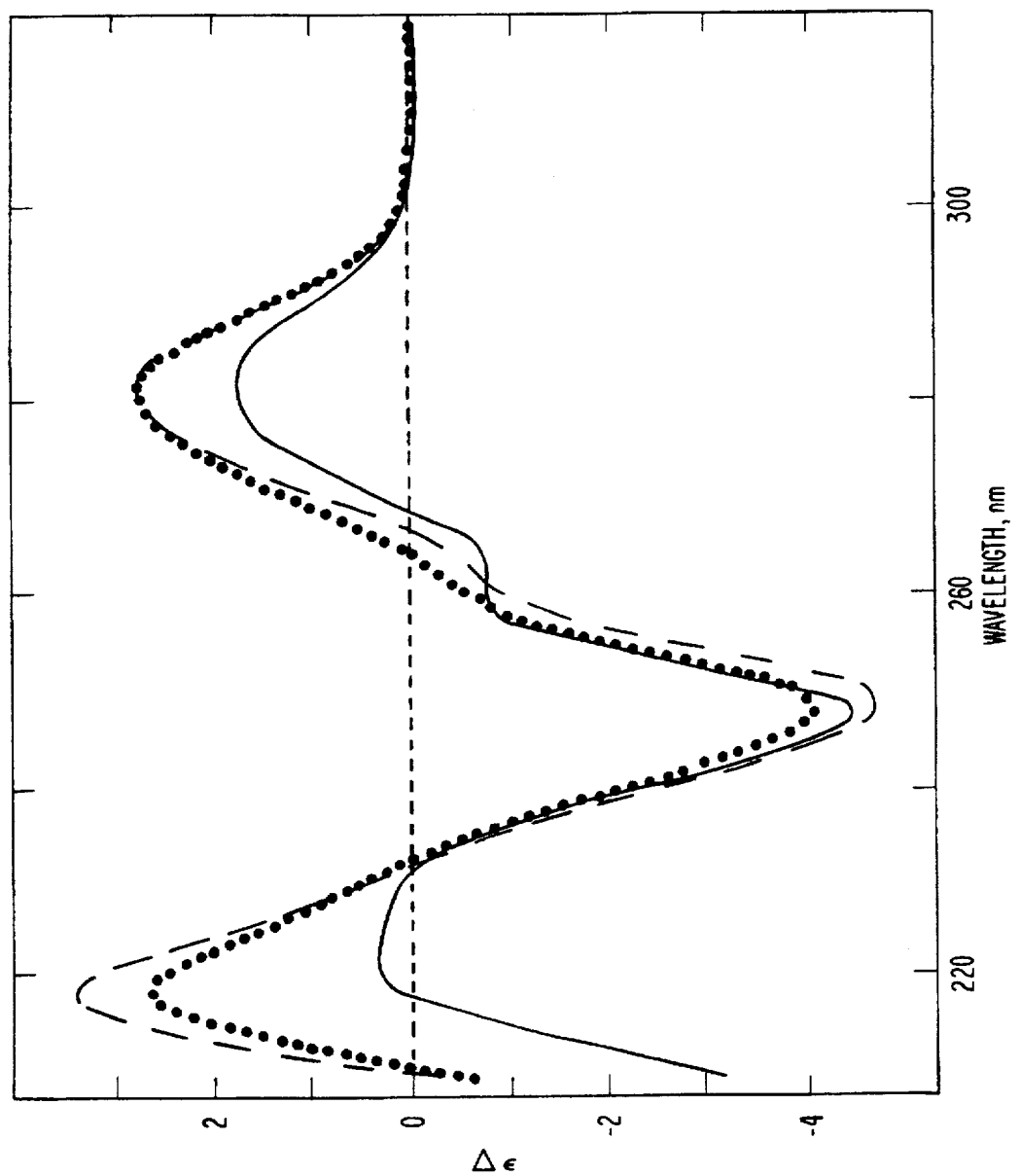

FORMATION OF TRIPLE HELIX COMPLEXES FOR THE DETECTION OF DOUBLE STRANDED DNA SEQUENCES USING OLIGOMERS WHICH COMPRISE AN 8-MODIFIED PURINE BASE

CROSS-REFERENCE TO RELATED APPLICATIONS

This application is a continuation of application Ser. No. 07/751,813, filed Aug. 30, 1991 now abandoned, which is a continuation-in-part of U.S. Ser. No. 368,027, filed Jun. 19, 1989 now abandoned, which is a continuation-in-part of U.S. Ser. No. 924,234, filed Oct. 28, 1986 now abandoned, the disclosures of which are incorporated herein by reference.

This invention was made with government support, including a grant from the National Institutes of Health, Contract Number GM-45012. The government has certain rights on the invention.

BACKGROUND OF THE INVENTION

Publications and other reference materials referred to herein are incorporated herein by reference and are numerically referenced in the following text and respectively grouped in the appended Bibliography which immediately precedes the claims.

The present invention is directed to novel methods of detecting and locating specific sequences in double stranded DNA using nucleoside oligomers which are capable of specifically complexing with a selected double stranded DNA Structure to give a triple helix structure.

Formation of triple helix structures by homopyrimidine oligodeoxyribonucleotides binding to polypurine tracts in double stranded DNA by Hoogsteen hydrogen bonding has been reported. (See, e.g. (1) and (2)). The homopyrimidine oligonucleotides were found to recognize extended purine sequences in the major groove of double helical DNA via triple helix formation. Specificity was found to be imparted by Hoogsteen base pairing between the homopyrimidine oligonucleotide and the purine strand of the Watson-Crick duplex DNA. Triple helical complexes containing cytosine and thymidine on the Hoogsteen (or third) strand have been found to be stable in acidic to neutral solutions, respectively, but have been found to dissociate on increasing pH. Incorporation of modified bases of T, such as 5-bromo-uracil and C, such as 5-methylcytosine, into the Hoogsteen strand has been found to increase stability of the triple helix over a higher pH range. In order for cytosine (C) to participate in the Hoogsteen-type pairing, a hydrogen must be available on the 3-N of the pyrimidine ring for hydrogen bonding. Accordingly, in some circumstances, C may be protonated at N-3.

DNA exhibits a wide range of polymorphic conformations, such conformations may be essential for biological processes. Modulation of signal transduction by sequence-specific protein-DNA binding and molecular interactions such as transcription, translation, and replication, are believed to be dependent upon DNA conformation. (3)

It is exciting to consider the possibility of developing therapeutic agents which bind to critical regions of the genome and selectively inhibit the function, replication, and survival of abnormal cells. (4) The design and development of sequence-specific DNA binding molecules has been pursued by various laboratories and has far-reaching implications for the diagnosis and treatment of diseases involving foreign genetic materials (such as viruses) or alterations in genomic DNA (such as cancer).

Nuclease-resistant nonionic oligodeoxynucleotides (ODN) consisting of a methylphosphonate (MP) backbone have been studied in vitro and in vivo as potential anticancer, antiviral and antibacterial agents. (5) The 5'-3' linked internucleotide bonds of these analogs closely approximate the conformation of nucleic acid phosphodiester bonds. The phosphate backbone is rendered neutral by methyl substitution of one anionic phosphoryl oxygen; decreasing inter- and intrastrand repulsion due to the charged phosphate groups. (5) Analogs with MP backbone can penetrate living cells and have been shown to inhibit mRNA translation in globin synthesis and vesicular stomatitis viral protein synthesis, and inhibit splicing of pre-mRNA in inhibition of HSV replication. Mechanisms of action for inhibition by the nonionic analogs include formation of stable complexes with complementary RNA and or DNA.

Nonionic oligonucleoside alkyl- and aryl-phosphonate analogs complementary to a selected single stranded foreign nucleic acid sequence can selectively inhibit the expression or function or expression of that particular nucleic acid without disturbing the function or expression of other nucleic acids present in the cell, by binding to or interfering with that nucleic acid. (See, e.g. U.S. Pat. Nos. 4,469,863 and 4,511,713). The use of complementary nuclease-resistant nonionic oligonucleoside methylphosphonates which are taken up by mammalian cells to inhibit viral protein synthesis in certain contexts, including Herpes simplex virus-1 is disclosed in U.S. Pat. No. 4,757,055.

The use of anti-sense oligonucleotides or phosphorothioate analogs complementary to a part of viral mRNA to interrupt the transcription and translation of viral mRNA into protein has been proposed. The anti-sense constructs can bind to viral mRNA and were thought to obstruct the cells ribosomes from moving along the mRNA and thereby halting the translation of mRNA into protein, a process called "translation arrest" or "ribosomal-hybridization arrest." (6)

The inhibition of infection of cells by HTLV-III by administration of oligonucleotides complementary to highly conserved regions of the HTLV-III genome necessary for HTLV-III replication and or expression is disclosed in U.S. Pat. No. 4,806,463. The oligonucleotides were found to affect viral replication and or gene expression as assayed by reverse transcriptase activity (replication) and production of viral proteins p15 and p24 (gene expression).

The ability of some antisense oligodeoxynucleotides containing internucleoside methylphosphonate linkages to inhibit HIV-induced syncytium formation and expression has been studied. (7)

Psoralen-derivatized oligonucleoside methylphosphonates have been reported capable of cross-linking either coding or noncoding single stranded DNA; however, double stranded DNA was not cross-linked. (28)

SUMMARY OF THE INVENTION

The present invention is directed to methods of detecting or recognizing a specific segment of double stranded nucleic acid or double stranded nucleic acid sequence and to methods of preventing expression or function of a specific segment of double stranded nucleic acid having a given sequence. This is achieved without destroying the intactness of the duplex structure or interrupting the base-pairing of the double stranded nucleic acid. The present invention is also directed to novel modified Oligomers which are useful for preventing expression and or functioning of a selected double stranded nucleic acid sequence and which optionally include a nucleic acid modifying group. Additionally, the present invention is directed to novel Oligomers which comprise purine nucleoside analogs wherein the purine base has been chemically modified to favor the syn conformation. The present invention is also directed to formation of a triple helix structure by the interaction of a specific segment of double stranded nucleic acid and such an Oligomer wherein the Oligomer is sufficiently complementary to the nucleic acid segment to read it and base pair (or hybridize) thereto. These double stranded nucleic acids include double stranded DNA, as well as DNA:RNA hybrids and double stranded RNA.

Accordingly, in one aspect, the present invention is directed to methods of detecting or recognizing a specific segment of double stranded nucleic acid which comprises contacting said segment of nucleic acid with an Oligomer of the present invention which is sufficiently complementary to the sequence of purine bases in said segment of double stranded nucleic acid or a portion thereof to hydrogen bond (or hybridize) therewith thereby giving a triple helix structure.

In one preferred aspect, the present invention is directed to methods of detecting or recognizing a specific segment of double stranded nucleic acid using an Oligomer which comprises at least one nucleosidyl unit which comprises a purine base modified to favor the syn conformation, preferably at the 8-position, and which is sufficiently complementary to said nucleic acid segment, or a portion thereof, to form a triple helix structure, wherein one strand of the duplex comprises a polypurine sequence of at least about 7 purine bases and wherein the Oligomer is parallel to the strand having the polypurine sequence. In this case, guanine in the polypurine sequence is ready by a base in the Oligomer selected from 8-oxo-adenine and cytosine or a cytosine analog either of which is protonated at N-3 at Physiological pH and adenine in the polypurine sequence is read by a base in the Oligomer selected from 8-oxo-guanine, thymine and uracil. According to a particularly preferred aspect, the polypurine sequence may include up to about 50% pyrimidine bases. In such case, cytosine in the polypurine sequence is read by a base in the Oligomer selected from 8-fluoroguanine, 8-fluoroadenine, 8-methoxyguanine and 8-azaguanine, and thymine or uracil in the polypurine sequence is read by a base in the Oligomer selected from 8-methoxyadenine and 8-azaadenine. The above-noted 8-modifications of the purine base favor the syn conformation.

In another aspect, the present invention is directed to methods of preventing or inhibiting expression or function of a specific segment of double stranded nucleic acid having a given sequence which comprises contacting said nucleic acid segment with an Oligomer of the present invention sufficiently complementary to said double stranded nucleic acid segment to form hydrogen bonds therewith, thereby giving a triple helix structure.

According to a preferred aspect of the above method, the invention is directed to methods of preventing or inhibiting expression or function of a specific segment of double stranded nucleic acid wherein one strand of the double stranded nucleic acid comprises a polypurine sequence of at least about 7 purine bases on one strand using an Oligomer which comprises at least one nucleosidyl unit which comprises a purine base modified to favor the syn conformation, preferably at the 8-position, and which Oligomer is parallel to the strand having the polypurine sequence. In this situation, guanine in the polypurine sequence is read by a base in the Oligomer selected from 8-oxo-adenine and cytosine or a cytosine analog either of which is protonated at N3 at physiological pH and adenine is read by a base in the Oligomer selected from 8-oxo-guanine, thymine and uracil. According to a particularly preferred aspect, the polypurine sequence may include up to about 50% pyrimidine bases. In such an instance, cytosine in the polypurine sequence is read by a base in the Oligomer selected from 8-fluoroguanine, 8-methoxyguanine and 8-azaguanine, and thymine or uracil in the polypurine sequence is read by a base in the Oligomer selected from 8-fluoroadenine, 8-methoxyadenine and 8-azaadenine. The above noted 8-modifications of the purine base favor the syn conformation.

The present invention is directed to methods wherein the nucleic acid segment comprises a gene in a living cell and wherein formation of the triple helix structure permanently inhibits or inactivates said gene.

In a preferred aspect, said Oligomer is modified to incorporate a nucleic acid modifying group which, after the Oligomer hydrogen bonds or hybridizes with the selected nucleic acid sequence, is caused to react chemically with the nucleic acid and irreversibly modify it. Such modifications may include cross-linking Oligomer and nucleic acid by forming a covalent bond thereto, alkylating the nucleic acid, cleaving said nucleic acid at a specific location, or by degrading or destroying the nucleic acid.

According to the present invention, third strand Oligomers are provided that comprise at least one nucleosidyl unit having a purine base which is modified to favor the syn conformation. These Oligomers comprise nucleosidyl units (or nucleoside monomers) which may be linked by any one of a variety of internucleosidyl linkages. These internucleosidyl linkages include, but are not limited to, phosphorus-containing linkages such as phosphodiester linkages, alkyl and aryl-phosphonate linkages, phosphorothioate linkages, phosphoramidite linkages and neutral phosphate ester linkages such as phosphotriester linkages; as well as internucleosidyl linkages which do not include phosphorus, such as morpholine linkages, formacetal linkages, sulfamate linkages, and carbamate linkages. Other internucleosidyl linkages known in the art may be used in these Oligomers. Also, according to a preferred aspect, these Oligomers may incorporate nucleosidyl units having modified sugar moieties which include ribosyl moieties, deoxyribosyl moieties and modified ribosyl moieties such as 2'-O-alkylribosyl (alkyl of 1 to 10 carbon atoms), 2'-O-arylribosyl, and 2'-halogen ribosyl, all optionally substituted with halogen, alkyl and aryl, and in particular, 2'-O-methylribosyl moieties. In particular, incorporation of nucleosidyl units having modified ribosyl, particularly 2'-O-methyl ribosyl, moieties may advantageously improve hybridization with the double stranded nucleic acid sequence and also improve resistance to enzymatic degradation.

In another aspect, the present invention provides novel nonionic alkyl- and aryl-phosphonate Oligomers comprising these purine nucleoside analogs which are sufficiently complementary to the purine sequence of a specific double stranded nucleic acid segment to hydrogen bond and form a triple helix structure. Preferred are nonionic methylphosphonate Oligomers.

The present invention also provides Oligomers having nucleosidyl units in which a cytosine analog replaces cytosine and wherein said cytosine analog comprises a heterocycle which has a hydrogen available for hydrogen bonding at the ring position which corresponds to N-3 of cytosine and which is capable of forming two hydrogen bonds with a guanine base at neutral pH. Such cytosine analogs include 5-methyl-cytosine, well as the analogs depicted in Table V.

In addition, the present invention is directed to Oligomers which comprise purine nucleoside analogs which can form a triplet with a purine-pyrimidine or pyrimidine-purine base pair, and to such Oligomers which can read a sequence on one strand of a duplex having both purine and pyrimidine nucleosides. In one preferred aspect, Oligomers are provided which comprise only purine nucleosides, including purine nucleoside analogs. In another preferred aspect, Oligomers are provided which comprise pyrimidine nucleosides in combination with these purine nucleoside analogs. These purine nucleoside analogs have been modified chemically, preferably at the 8-position, so that the syn conformation is favored. Accordingly such purine analogs nucleoside include 8-oxo-A, 8-oxo-G, 8-fluoro-A, 8-fluoro-G, 8-methoxy-A, 8-methoxy-G, 8-aza-A and 8-aza-G.

(A) Definitions

As used herein, the following terms have the following meanings unless expressly stated to the contrary.

The term "purine" or "purine base" includes not only the naturally occurring adenine and guanine bases, but also modifications of those bases such as bases substituted at the 8-position.

The term "nucleoside" includes a nucleosidyl unit and is used interchangeably therewith, and refers to a subunit of a nucleic acid which comprises a 5 carbon sugar and a nitrogen-containing base. The term includes not only units having A, G, C, T and U as their bases, but also analogs and modified forms of the bases (such as 8-substituted purines). In RNA the 5 carbon sugar is ribose; in DNA, it is a 2'-deoxyribose. The term also includes analogs of such subunits, including modified sugars such as 2'-O-alkyl ribose.

The term "phosphonate" refers to the group

groups include those which do not sterically hinder the phosphonate linkage or interact with each other. The phosphonate group may exist in either an "R" or an "S" configuration. Phosphonate groups may be used as internucleosidyl phosphorus group linkages (or links) to connect nucleosidyl units.

The term "phosphodiester" refers to the group O=P—O wherein phosphodiester groups may be used as internucleosidyl phosphorus group linkages (or links) to connect nucleosidyl units. A "non-nucleoside monomeric unit" refers to a monomeric unit which does not significantly participate in hybridization of an Oligomer to a target sequence. Such monomeric units must not, for example, participate in any significant hydrogen bonding with a nucleoside, and would exclude monomeric units having as a component, one of the 5 nucleotide bases or analogs thereof.

A "nucleoside/non-nucleoside polymer" refers to a polymer comprised of nucleoside and non-nucleoside monomeric units.

The term "oligonucleoside" or "Oligomer" refers to a chain of nucleosides which are linked by internucleoside linkages which is generally from about 6 to about 100 nucleosides in length, but which may be greater than about 100 nucleosides in length. They are usually synthesized from nucleoside monomers, but may also be obtained by enzymatic means. Thus, the term Oligomer refers to a chain of oligonucleosides which have internucleosidyl linkages linking the nucleoside monomers and thus, includes oligonucleotides, nonionic oligonucleoside alkyl- and aryl-phosphonate analogs, alkyl- and aryl-phosphonothioates phosphorothioate analogs of oligonucleotides, phosphoramidate analogs of oligonucleotides, neutral phosphate ester oligonucleoside analogs, such as phosphotriesters and other oligonucleoside analogs and modified oligonucleosides, and also includes nucleoside/non-nucleoside polymers. The term also includes nucleoside/non-nucleoside polymers wherein one or more of the phosphorous group linkages between monomeric units has been replaced by a non-phosphorous linkage such as a, morpholino linkage, a formacetal linkage, a sulfamate linkage or a carbamate linkage.

The term "alkyl- or aryl-phosphonate Oligomer" refers to Oligomers having at least one alkyl- or aryl-phosphonate internucleosidyl linkage.

The term "methylphosphonate Oligomer" (or "MP-Oligomer") refers to Oligomers having at least one methylphosphonate internucleosidyl linkage.

The term "neutral Oligomer" refers to Oligomers which have nonionic internucleosidyl linkages between nucleoside monomers (i.e. linkages having no net positive or negative ionic charge) and include, for example, Oligomers having internucleosidyl linkages such as alkyl- or aryl-phosphonate linkages, alkyl- or aryl-phosphonothioates, neutral phosphate ester linkages such as phosphotriester linkages, especially neutral ethyltriester linkages; and non-phosphorus-containing internucleosidyl linkages, such as sulfamate, morpholino, formacetal and carbamate linkages. Optionally, a neutral Oligomer may comprise a conjugate between a oligonucleoside or nucleoside/non-nucleoside polymer and a second molecule which comprises a conjugation partner. Such conjugation partners may comprise intercalators, alkylating agents, binding substances for cell surface receptors, lipophilic agents, photo-cross-linking agents such as psoralen, and the like. Such conjugation partners may further enhance the uptake of the Oligomer, modify the interaction of the Oligomer with the target sequence, or alter the pharmacokinetic distribution of the Oligonucleoside. The essential requirement is that the oligonucleoside or nucleoside non-nucleoside polymer that the conjugate comprises be neutral.

The term "neutral alkyl- or aryl-phosphonate Oligomer" refers to neutral oligomers having neutral internucleosidyl linkages which comprise at least one alkyl- or aryl- phosphonate linkage.

The term "neutral methylphosphonate Oligomer" refers to neutral Oligomers having internucleosidyl linkages which comprise at least one methylphosphonate linkage.

The term "Third Strand Oligomer" refers to Oligomers which are capable of reading a segment of a double stranded nucleic acid, such as a DNA duplex, and forming a triple helix structure therewith.

The term "complementary" when referring to an Oligomer Third Strand refers to Oligomers having base sequences which hydrogen bond (and base pair or hybridize) with the purine base of a corresponding (Watson-Crick) base pair of a double stranded DNA to form a triple helix structure.

In the various Oligomer sequences listed herein "p" in, e.g., as in ApA represents a phosphodiester linkage, and " p̲" in, e.g., as in CpG represents a methylphosphonate linkage. Also, notation such as "T̲" indicates nucleosidyl groups linked by methyl phosphonate linkages.

The term "read" refers to the ability of a nucleic acid residue to recognize through hydrogen bond interactions the base sequence of another nucleic acid. Thus, in reading a double stranded DNA sequence, a Third Strand Oligomer is able to recognize through hydrogen bond interactions the base pairs, in particular the purine bases, in the duplex of a segment of double stranded DNA.

The term "triplet" refers to a situation such as that depicted in FIGS. 1A, 1B; 2A to 2D and 7 to 10, wherein a base in the Third Strand has hydrogen bonded (and thus base paired) with a (Watson-Crick) base pair of a segment of double stranded DNA.

BRIEF DESCRIPTION OF THE DRAWINGS

FIG. 1A depicts a triplet wherein a pyrimidine base in the Third Strand forms a triplet with a duplex DNA (Watson-Crick) base pair.

FIG. 1B depicts a triplet wherein a pyrimidine base in the Third Strand forms a triplet with a duplex DNA (Watson-Crick) base pair.

FIG. 3A depicts the base sequences of exemplary polypurine sequence triple helix structures wherein the Third Strand "reads" and, thus, base pairs with purine bases on one strand of a double stranded DNA.

FIG. 3B depicts the base sequences of exemplary polypurine sequence triple helix structures wherein the Third Strand "reads" and, thus, base pairs with purine bases on one strand of a double stranded DNA.

FIG. 4A depicts the base sequences of exemplary mixed sequence triple helix structures wherein the Third Strand "reads" and, thus, base pairs with purine bases on both strands of a double stranded DNA.

FIG. 4B depicts the base sequences of exemplary mixed sequence triple helix structures wherein the Third Strand "reads" and, thus, base pairs with purine bases on both strands of a double stranded DNA.

FIG. 4C depicts the base sequences of exemplary mixed sequence triple helix structures wherein the Third Strand "reads" and, thus, base pairs with purine bases on both strands of a double stranded DNA.

FIG. 4D depicts the base sequences of exemplary mixed sequence triple helix structures wherein the Third Strand "reads" and, thus, base pairs with purine bases on both strands of a double stranded DNA.

FIG. 4E depicts the base sequences of exemplary mixed sequence triple helix structures wherein the Third Strand "reads" and, thus, base pairs with purine bases on both strands of a double stranded DNA.

FIG. 5 depicts a nucleosidyl unit having a modified sugar moiety with an alkyleneoxy link for lengthening internucleoside phosphorus linkages and processes for its preparation.

FIG. 13B depicts observed circular dichroism spectra of a solution containing 1.6 μM I(OA) and 1.6 μM II•III (G•C) at 10° C. (——) and 35° C. (· · · ·) and the calculated weighted average spectra of 1.6 μM I(OA) and 1.6 μM II•III (G•C) at 10° C. (– – – –). All were performed in standard buffer.

DETAILED DESCRIPTION OF THE INVENTION

Figure 2A:
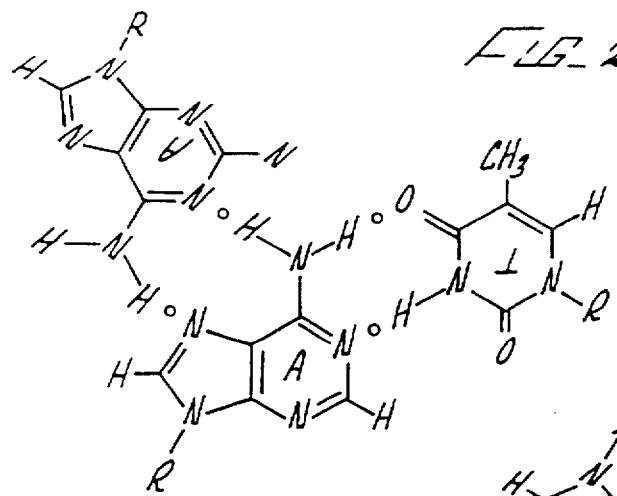
FIG. 2A depicts a triplet wherein the purine base in the Third Strand forms a triplet with a duplex DNA (Watson-Crick) base pair.

The present invention involves the formation of triple helix structures with a selected double stranded DNA sequence by contacting said DNA with an Oligomer which is sufficiently complementary to the purine sequence of the double stranded DNA to form hydrogen bonds (or hybridize) therewith.

(A) General Aspects

In addition to other aspects described herein, this invention includes the following aspects.

(I) A first aspect concerns the reading (or recognition) of the base pairs in the double stranded DNA segment without opening the base pair, through the hydrogen bond formation by the bases in the Third Strand with the extra hydrogen bond sites of purines in the double stranded DNA, such as adenine and guanine. In other words, the reading of the base pair sequence in the DNA duplex is always done by reading the purine of the base pair, through hydrogen bond formation with the bases in the Third Strand, with the remaining available hydrogen bonding sites of the purines in the DNA. Either purines (such as adenine (A) or guanine (G)) or pyrimidines (thymine (T) or cytosine (C)) in the Third Strand can form hydrogen bonds with the purines in the DNA, i.e.:

i) Adenine (A) in the base pair of DNA can be read or hydrogen bonded with A or T in the Third Strand, or in a preferred aspect, A is read by 8-oxo-G.
 ii) Guanine (G) in the base pair of DNA can be read or paired with C or G in the Third Strand, or in a preferred aspect, G is read by 8-oxo-A.

In one preferred aspect of the present invention, the phosphorus-containing backbone of the Third Strand comprises methylphosphonate groups as well as naturally occurring phosphodiester groups.

(II) A second aspect of this invention is to read the purine (A or G) in the double stranded DNA totally by the use of purine bases from the Third Strand. The polarity of the strands, either the anti-parallel or parallel direction of the Third Strand in respect to the strand containing the purine to be read in the duplex is important.

The base planes of the purines and pyrimidines are rigid, and the furanose ring only allows a small ripple (about 0.5 Å above or below the plane). Thus, the conformational state of the nucleoside is defined principally by the rotation of these two more or less rigid planes, i.e. the base and the pentose, relative to each other about the axis of the C'-1 to N-9 or N-1 bond. The sugar-base torsion angle, $\phi_{CN}$, has been defined as "the angle formed by the trace of the plane of the base with the projection of the C-1' to O-1' bond of the furanose ring when viewed along the C'-1 to a bond. This angle will be taken as zero when the furanose-ring oxygen is antiplanar to C-2 of the pyrimidine or purine ring and positive angles will be taken as those measured in a clockwise direction when viewing C-1' to N." This angle has also been termed the glycosyl torsion angle. Using the above definition, it was concluded that there were two ranges of $\phi_{CN}$ for the nucleosides, about $-30°$ for the anti conformation and about $+150°$ for the syn conformation. The range for each conformation is about ±45°. (22, 22a) Other researchers have used or proposed slightly different definitions of this angle. (23,24,25,26,27) Information concerning $\phi_{CN}$ has been obtained using procedures such as X-ray diffraction, proton magnetic resonance (PMR) and optical rotatory dispersion-circular dichroism (ORD-CD). (22a)

In order to accommodate the Change of location of the purine base to be read from one strand (termed the "Watson strand") to the opposite strand (termed the "Crick strand"), we have recognized that a particular conformation of the nucleoside, defined by the torsion angle of the glycosyl bond, of the purine nucleosidyl unit in the Third Strand is required in order that the purine nucleoside in the Third Strand can be used to read the purine in the duplex. In other words, in order to read the purine bases in the DNA, the conformations of the purine nucleosidyl units in the Third Strand are influenced by the polarity (parallel (5' to 3') or anti-parallel (3' to 5') direction) of the strand containing the purine bases to be read in the DNA in relation to the Third Strand. For the purine nucleosidyl units in the Third Strand, reading the purine in the parallel strand in the duplex, the conformation of the purine nucleosidyl unit in the Third Strand should be in the syn conformation. On the other hand, the conformation of the purine nucleosidyl unit in the Third Strand in reading the corresponding purine in the anti-parallel strand in the duplex, should exist in anti conformation. Thus, in reading the purine bases in the duplex distributed in both strands, one has the choice of using a Third Strand which has the same polarity as (i.e. is parallel to) either one strand or the opposite strand. As an example,

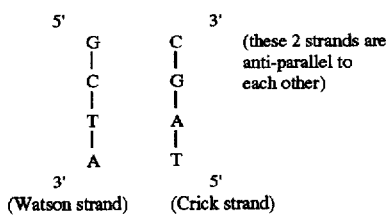

The sequence of the Third Strand in the triplet with the DNA duplex having the same polarity of the Watson strand from 5' to 3' would be as follows:

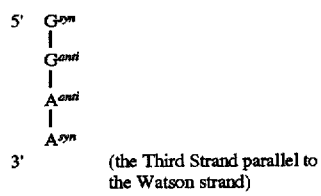

(the Third Strand parallel to the Watson strand)

The sequence of a Third Strand parallel to the Crick strand would be as follows:

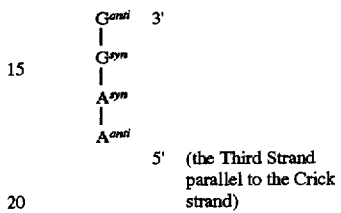

(the Third Strand parallel to the Crick strand)

According to one aspect of this invention, in constructing the Third Strand for reading the purines in the base pairs of the duplex, the following guidelines apply:

(i) Starting from the 5' end toward the 3' end, the purine nucleosidyl units (A or G) of the Third Strand need to be in syn conformation in reading the purines in the base pair (A or G) of the parallel ("Watson") strand of the double stranded DNA. In reading the second purine in the second base pair, the same requirement applies if the purine is located in the same strand as the first purine. However, if the second purine is located in the opposite anti-parallel ("Crick") strand (now the opposite strand is anti-parallel to the Third Strand), the purine nucleosidyl unit needs to be in anti conformation. In all cases, adenine in the Third Strand is used to read adenine in the duplex and guanine in the Third Strand is used to read guanine in the duplex.

Figure 6:
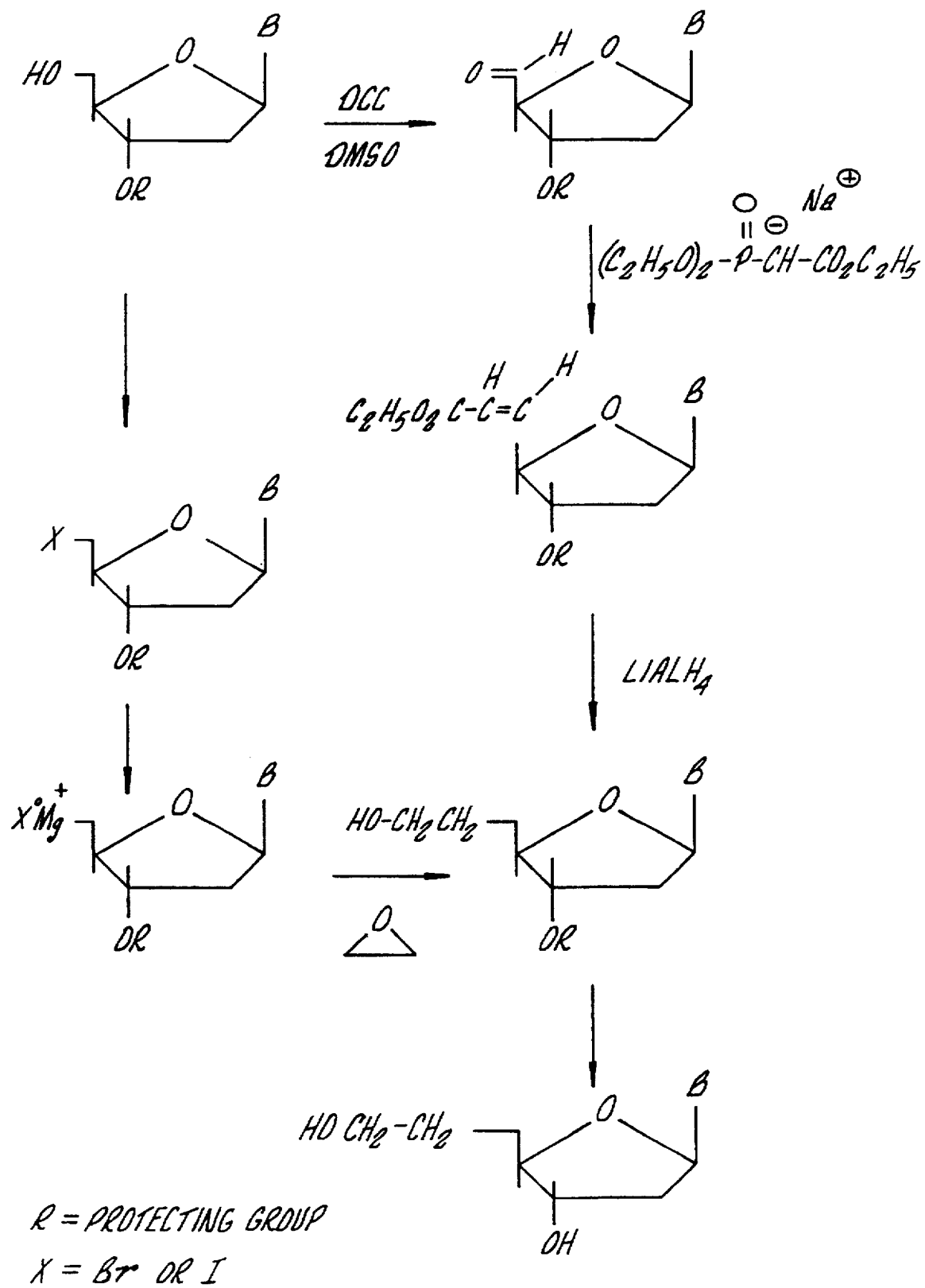
FIG. 6 depicts a nucleosidyl unit having a modified sugar moiety with an alkylene link for lengthening internucleoside phosphorus linkages and processes for its synthesis.

(ii) In order to be able to "read" (or base pair) with purine bases on either strand of a double stranded nucleic acid, the distance between nucleosidyl units along the phosphorus backbone of the Third Strand must be increased. Two examples of types of lengthening link formats for the phosphorus backbone are proposed. One type of link format for the phosphorus backbone would use a universal lengthening link on the individual nucleosidyl Units, i.e. all the lengthening links of the Third Strand would be the same. Such a universal link format is particularly suitable for Third Strands comprising only purine bases. Accordingly, the length of the link between the 5' carbon of the "nucleosidyl unit one" to the 3' oxygen of the subsequent "nucleosidyl unit two" may be increased by two atoms (such as —$CH_2CH_2$—) or by 3 atoms (such as —$O-CH_2-CH_2$—), thereby lengthening the linkage between individual nucleosidyl units by 2 to 6 Å. In order to allow an appropriate distance between nucleosidyl units, we recommend that separation of the units be increased by a number of atoms ranging from 1 to 6. FIG. 6 illustrates an example of a nucleosidyl unit comprising this lengthening link format and proposed synthetic routes.

A second lengthening link format for the phosphorus backbone would comprise non-uniform lengthening links. Links having internucleosidyl distances on the order of the standard phosphodiester backbone for the Third Strand would be employed when the purines being read were on the same strand, while a lengthened link (15–17 Å in length) which could comprise lengthening links on the 3' carbon of one nucleosidyl unit and on the 5'-carbon of its neighbor, would be employed to read the purine bases located on opposite strands. Such a non-uniform lengthening link format would be particularly suitable for use in Third Strands comprising both pyrimidine (or pyrimidine analog) and purine bases.

(III) It has been thought that reading the base pair sequence in the nucleic acid duplex was always done by reading the purine of the base pair, through hydrogen bond formation by the bases of the Third Strand with the remaining available hydrogen bonding sites of the purines in the DNA. Thus, in order for a Third Strand Oligomer to be able to form a triplex without having to switch strands, homopurine tracts in one of the strands of the duplex were required. Reading of (duplex) sequences which comprised purine pyrimidine mixtures would require use of lengthening links in the Third Strand Oligomer so that the Oligomer could read purine bases on both strands.

However, according to the present invention, there are provided Third Strand Oligomers which can read both purine and pyrimidine bases, by hydrogen bond formation with the bases in the Third Strand with available hydrogen bonding sites of both purine and pyrimidine bases in the double stranded nucleic acid. This allows the Oligomer to read a sequence such as one where a homopurine run is interrupted by one or more pyrimidines bases without necessitating use of a lengthening link on the Third Strand Oligomer to allow for switching strands which are read at a site of a pyrimidine interruption, so that the purine on the other strand could be read to give the triplex. Use of these Oligomers is advantageous in that only one strand need be read. Reading of only one strand also simplifies synthesis of the Third Strand Oligomers.

These Oligomers are parallel to and, thus, have the same polarity as the strand of these double stranded nucleic acid that is being read. The purine analogs used in these Third Strand Oligomers are in the syn configuration.

Thus, according to the present invention, Oligomers are provided wherein 8-oxo-adenine is used to complex with (or read) G, 8-oxo-guanosine is used to complex with (or read) A, 8-fluoro G is used to read C and 8-fluoro A is used to read T (or U?). Thus, all four bases in DNA on the same strand of the double stranded nucleic acid DNA can be read using these Oligomers.

(B) Formation of Triple Helix Structures (I) Triplet (or Triple-Stranded) base pairing (a) Pyrimidine in Third Strand Forming Triplet In one aspect of the present invention, triplets are formed wherein a pyrimidine base in the Third Strand forms hydrogen bonds and, thus, base pairs with the purine base of a base pair of the double stranded DNA sequence. Examples of such triplets where having a pyrimidine base as the base in the Third Strand are shown in FIGS. 1A and 1B.

FIG. 1A depicts a triplet having T as the Third Strand base which forms hydrogen bonds and, thus, base pairs with the A of the double stranded DNA. In such circumstances, the T of the Third Strand is aligned parallel to the A-containing strand of the double stranded DNA, and anti-parallel to the T-containing strand of the double stranded DNA (which is also anti-parallel to the A-containing strand). Accordingly, the sequence for that triplet is written as follows:

T A⊥

FIG. 1B depicts a triplet having a protonated cytosine (C+) as the Third Strand base which forms hydrogen bonds and, thus, base pairs with a G of a G-C base pair in the double stranded DNA. In such circumstance, the cytosine base in the Third Strand must be protonated at N3 in order to form hydrogen bonds necessary for a stable triplet. Optionally, a cytosine may be replaced with a cytosine analog having a quaternary nitrogen at a position analogous to N3. In the triplet depicted, the C+ (or its analog) of the Third Strand is aligned parallel to the G-containing strand of the double stranded DNA, and anti-parallel to the C-containing strand of the double stranded DNA (which is also anti-parallel to the G-containing strand). Accordingly, such a triplet sequence is written as follows:

C+ G ⊃

(b) Adenine or Guanine in Third Strand Forming Triplet

In another aspect of the present invention, triplets are formed wherein a purine base in the Third Strand forms hydrogen bonds with and, thus, base pairs with the same purine base in one strand of the double stranded DNA. Accordingly, A will pair with A and G will pair with G.

In contrast to the pyrimidine Third Strand triplets, the purine base in the Third Strand is capable of base pairing with the purine base of double stranded DNA such that the strand polarity of the Third Strand containing the purine base may be aligned either parallel or anti-parallel to strand polarity of the strand containing the purine to be read in the double stranded DNA.

For example, FIG. 2A depicts a triplet where the 1A of the Third Strand is aligned parallel to the A of the double stranded DNA, and anti-parallel to the T of the double stranded DNA. In such a circumstance, the glycosyl (C-N) torsion angle of the Third Strand A is in the syn conformation, and the glycosyl torsion angles of the A and T bases of the double stranded DNA are both in the anti conformation. Such a triplet sequence is written as follows:

A A⊥

Figure 2B:
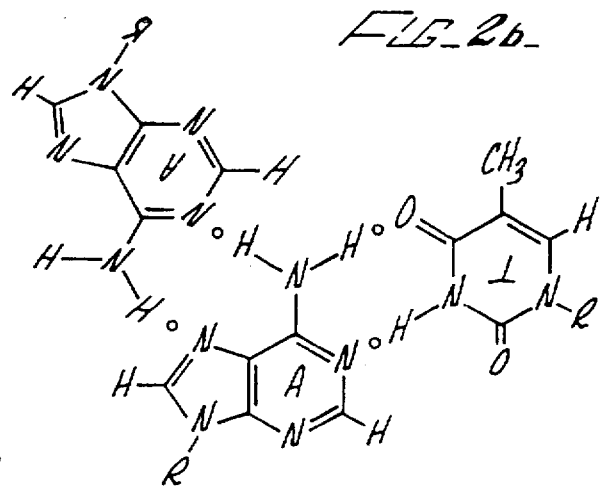
FIG. 2B depicts a triplet wherein the purine base in the Third Strand forms a triplet with a duplex DNA (Watson-Crick) base pair.

Alternatively, FIG. 2B depicts a triplet where the A of the Third Strand is aligned anti-parallel to the A of the double stranded DNA and parallel to the T of the double stranded DNA. In such circumstance, the glycosyl torsion angles of all three bases are in the anti conformation. Such a triplet sequence is written as follows:

∀ A⊥

Figure 2C:
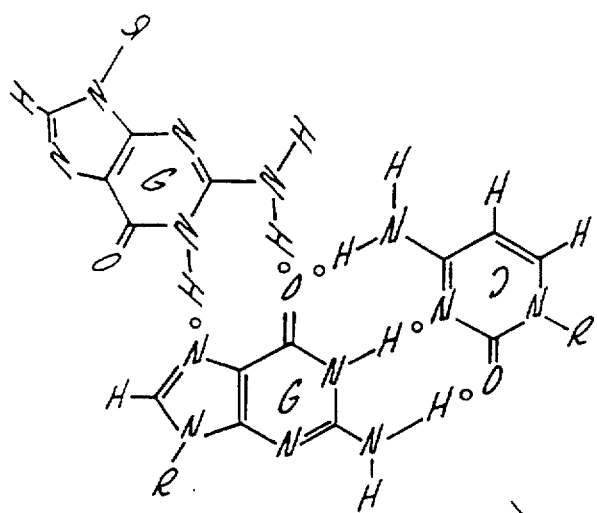
FIG. 2C depicts a triplet wherein the purine base in the Third Strand forms a triplet with a duplex DNA (Watson-Crick) base pair.

FIG. 2C depicts a triplet wherein the G of the Third Strand is aligned parallel to the G of the double stranded DNA, and anti-parallel to the C of the double stranded DNA. In such circumstance, the glycosyl torsion angle of the Third Strand G is in the syn conformation, and the glycosyl torsion angles of the G-C bases of the double stranded DNA are both in the anti conformation. Such a triplet sequence is written as follows:

GGC

Figure 2D:
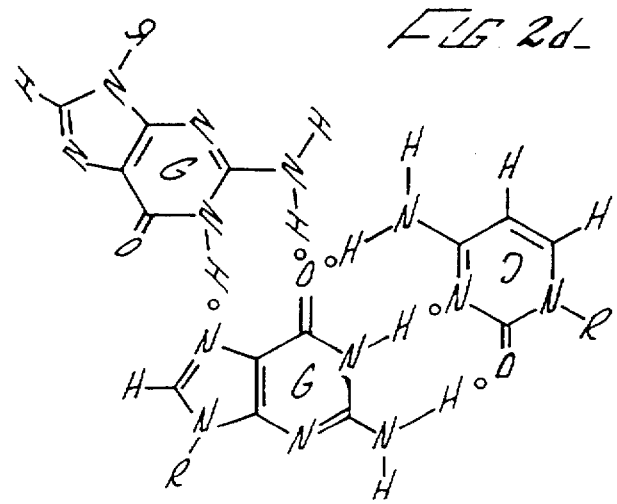
FIG. 2D depicts a triplet wherein the purine base in the Third Strand forms a triplet with a duplex DNA (Watson-Crick) base pair.

FIG. 2D depicts a triplet wherein the G of the Third Strand is aligned anti-parallel to the G of the double stranded DNA and parallel to the C of the double stranded DNA. In such circumstance, the glycosyl torsion angles for all three bases are in the anti conformation. Such a triplet sequence is written as follows:

ɔGC (c) Purine Analog in Third Strand Forming Triplet

According to a preferred aspect of the present invention, triplets are formed using a Third Strand Oligomer which comprises a nucleoside which comprises a purine analog which has been chemically modified to favor the base being in the syn configuration. According to this aspect, the Third Strand Oligomer is parallel to the strand of the double-stranded nucleic acid being read.

Certain of these purine analogs are capable of hydrogen bonding with the purine base of a double-stranded nucleic acid and, thus, forming a triplet such that the strand polarity of the third strand is aligned parallel to the strand polarity of the strand containing the purine to be read in the double stranded nucleic acid. In addition, certain other of these purine analogs are capable of hydrogen bonding with the pyrimidine base of a double-stranded nucleic acid and, thus, forming a triplet such that the strand polarity of the third strand is aligned parallel to the strand polarity of the strand containing the pyrimidine to be read in the double-stranded nucleic acid. Since the purine bases to be read have more sites available for hydrogen bonding than do the pyrimidine bases, it is preferred that the sequence to be read on one strand of the double stranded DNA comprises mostly purine bases, at least 50% or more purine bases.

Figure 7:
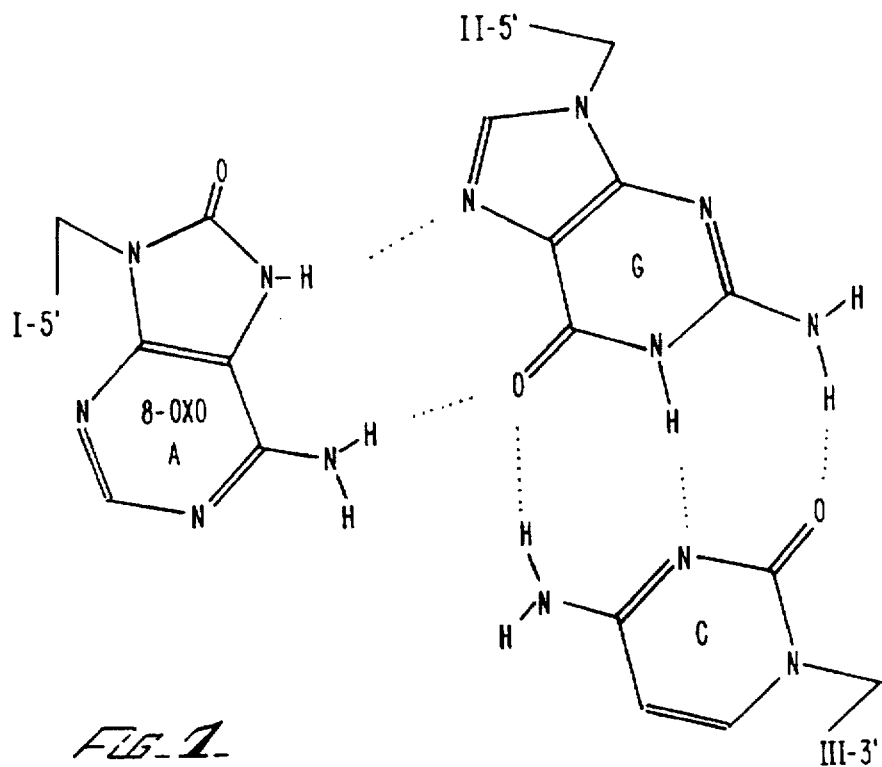
FIG. 7 depicts a triplet wherein 8-oxo-A in the third strand forms a triplet with the G of a G-C (Watson-Crick) base pair.

FIG. 7 depicts a triplet wherein an 8-oxo-A of the third strand is aligned parallel to G of the double-stranded nucleic acid and antiparallel to the C of the double-stranded nucleic acid. In such a circumstance the glycosyl (C-N) torsion angle of the third strand 8-oxo-A is in the syn conformation, and the glycosyl torsion angles of the G and C bases of the double-stranded nucleic acid are both in the anti-conformation.

Figure 8:
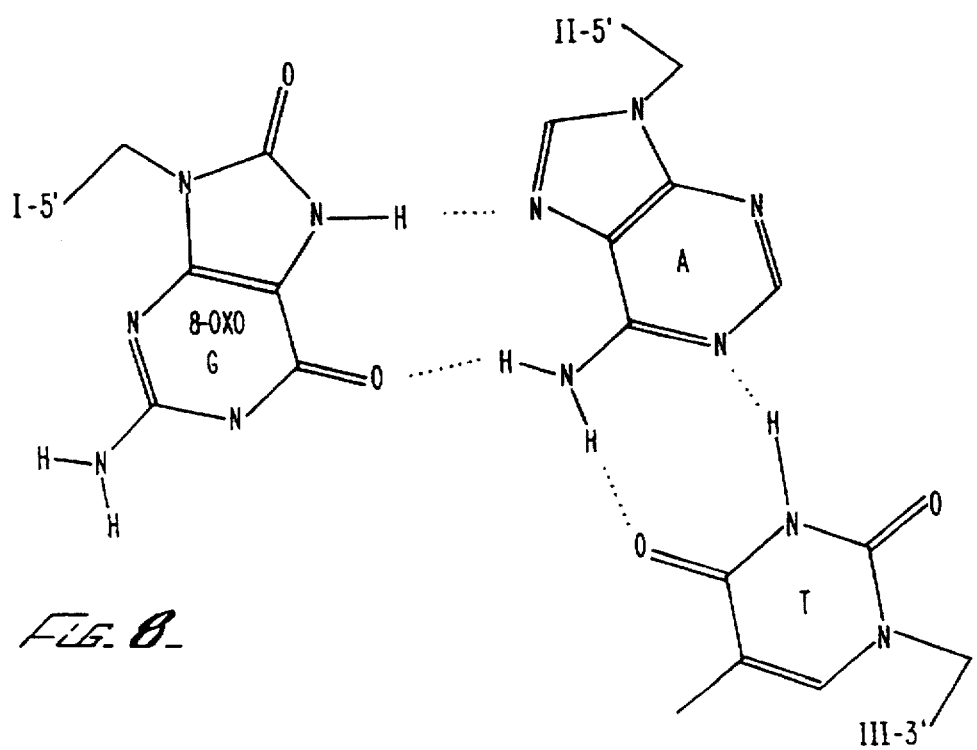
FIG. 8 depicts a triplet wherein 8-oxo-G in the Third Strand forms a triplet with the A of an A-T (Watson-Crick) base pair.

FIG. 8 depicts a triplet wherein an 8-oxo-G of the third strand is aligned parallel to A of the double stranded nucleic acid and antiparallel to the T or U of the double stranded nucleic acid. In such circumstances, the glycosyl (C-N) torsion angle of the third strand 8-oxo-G is in the syn configuration and the glycosyl torsion angles of the A and T or U bases of the double stranded nucleic acid are both in the anti-conformation.

Figure 9:
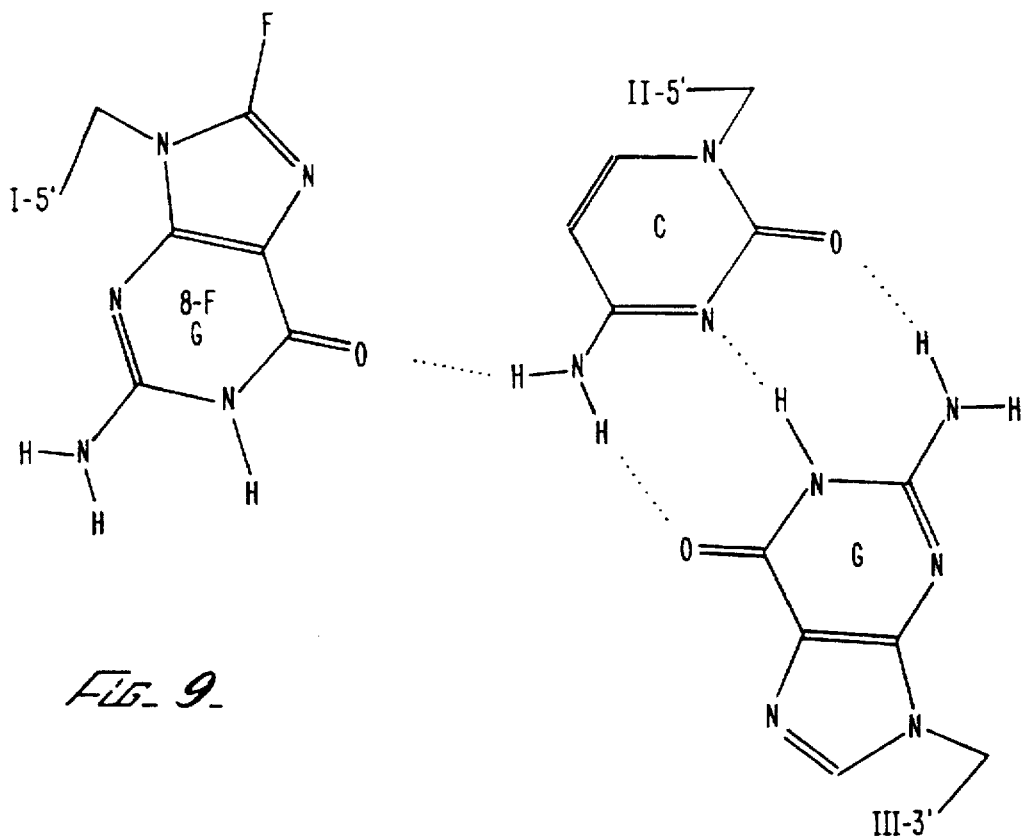
FIG. 9 depicts a triplet wherein 8-fluoro G in the Third Strand forms a triplet with the C of a C-G (Watson-Crick) base pair.

FIG. 9 depicts a triplet wherein an 8-fluoro G in the third strand is aligned parallel to the C of the double stranded nucleic acid. In such a circumstance, the glycosyl (C-N) torsion angle of the third strand 8-fluoro G is in the syn conformation and the glycosyl torsion angles of the C and G bases of the double-stranded nucleic acid are both in the anti-conformation.

Figure 10:
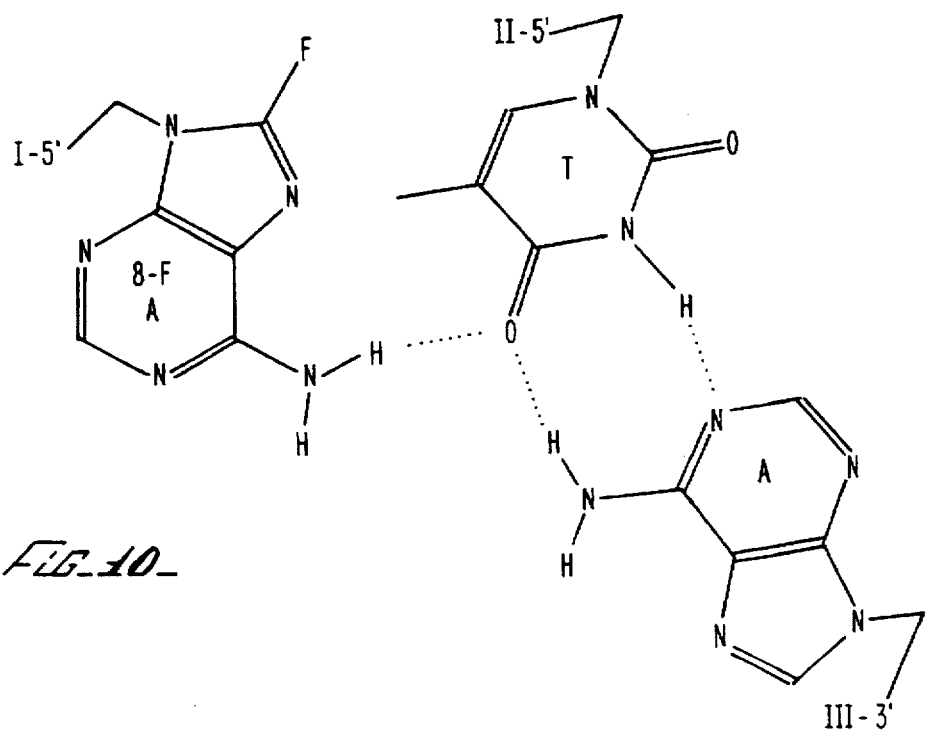
FIG. 10 depicts a triplet wherein 8-fluoro A in the Third Strand forms a triplet with the T of a T-A (Watson-Crick) base pair.

FIG. 10 depicts a triplet wherein an 8-fluoro-A in the third strand is aligned parallel to the T (or U) of a double stranded nucleic acid. In Such a circumstance, the glycosyl (C-N) torsion angle of the third strand 8-fluoro-A is in the syn conformation and the glycosyl torsion angles of the A and T (or U) bases of the double stranded nucleic acid are both in the anti-conformation.

(1) Polypurine Sequences

Where one strand of a selected double stranded nucleic acid sequence comprises a polypurine sequence comprising all purine bases, an Oligomer complementary to the polypurine sequence is used and may comprise a complementary sequence of pyrimidines or purines or a mixture thereof. Preferred Oligomers, include nonionic MP-Oligomers which are nuclease resistant and are capable of forming the previously-discussed triplet structures with the double stranded nucleic acid.

Examples of triple stranded helix sequences wherein the Third Strand hinds to a polypurine sequence in one strand of a double stranded nucleic acid sequence are schematically depicted in FIG. 3A to 3C. In FIGS. 3A to 3C, C$^+$ denotes a protonated C.

Mixed Sequinces

Mixed sequences are sequences wherein the purine bases of the selected nucleic acid sequence are located on both strands of the double stranded nucleic acid. In one type of instance the polypurine sequence on one strand of the double-stranded nucleic acid sequence may comprise up to about 50% pyrimidine bases.

Where only purine bases are read, the Third Strand Oligomer must be able to hydrogen bond and, thus, base pair with the purine base of each base pair of the double stranded nucleic acid sequence without regard to which strand of the double stranded nucleic acid the purine base is located on. Accordingly, the Third Strand Oligomer must be able to "read" across the double stranded nucleic acid. Examples of mixed sequences including an appropriately complementary Third Strand are depicted in FIG. 4A to 4E.

Figures 4A, 4B, 4C, 4D, 4E:
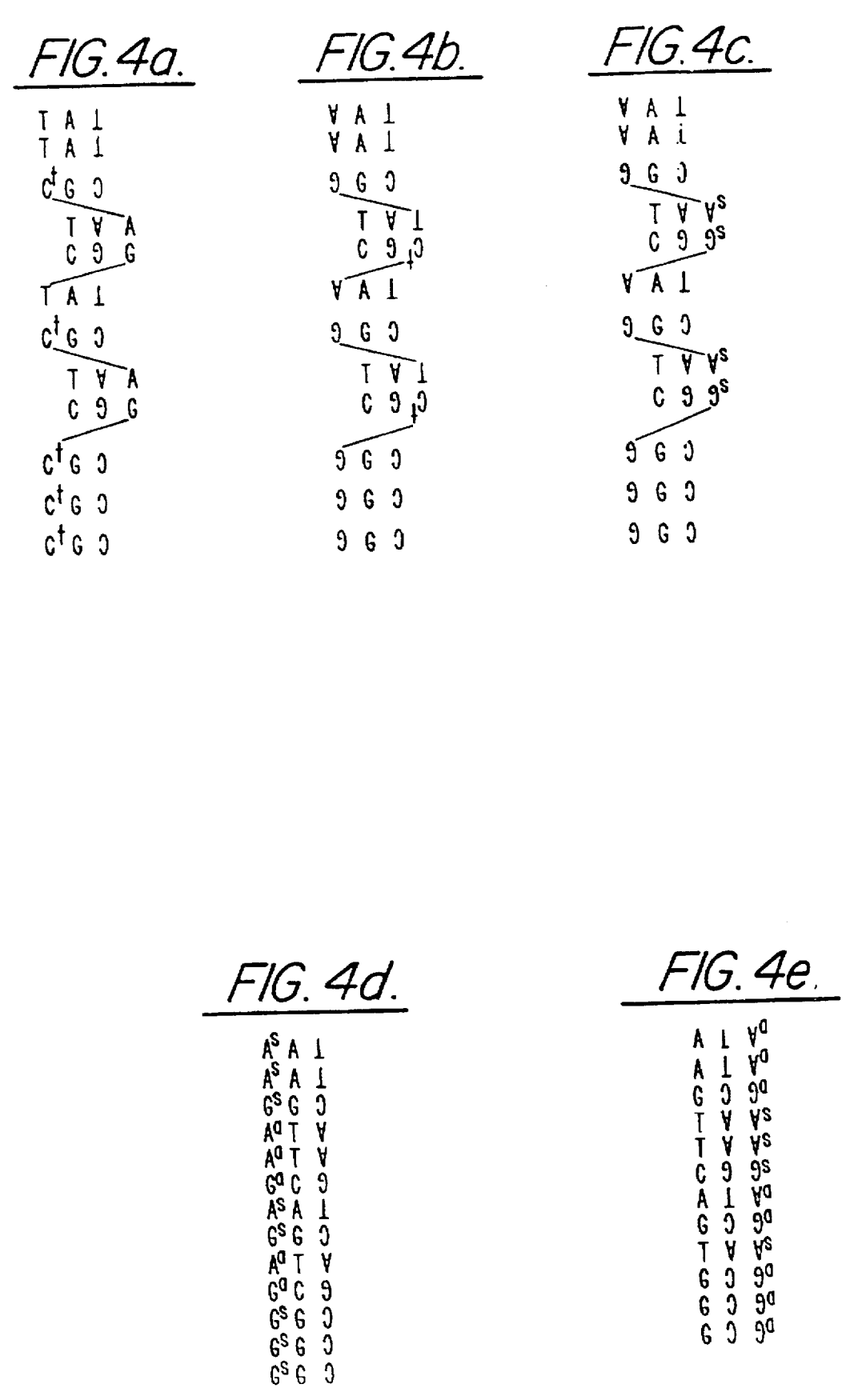

FIG. 4A depicts a mixed sequence having a pyrimidine-rich Third Strand.

FIG. 4B depicts a mixed sequence having a purine-rich Third Strand.

FIG. 4C, 4D and 4E depict mixed sequences having Third Strands containing only purine bases. In FIGS. 4C to 4E, "S" denotes syn and "a" denotes anti; no superscript denotes anti.

Where the Third Strand Oligomer must "read" across the double strand from one strand to the opposite strand in order to base pair with the purine base, it may be advantageous to provide a lengthened internucleosidyl phosphorus linkage by incorporation of the previously-described backbone link formats into the phosphorus backbone which connects the sugar moieties of the nucleosidyl units.

For example, an internucleosidyl linkage may be lengthened by the interposition of an appropriate alkylene (—(CH$_2$)$_n$—) or alkyleneoxy (—(CH$_2$)$_n$O—) lengthening link between the 5'-carbon and the 5' hydroxyl of the sugar moiety of a nucleosidyl unit or a similar link between the 3'-carbon and the 3'-hydroxyl. (See FIGS. 5 and 6). Where indicated, such lengthening links may be interposed at both the 3'- and 5'-carbons of the sugar moiety.

Where consecutive purines of the selected double stranded DNA sequence occur on the same strand, such lengthening links need not be employed; internucleosidyl phosphorus linkages such as methylphosphonate linkages allow an appropriate base on the Third Strand to read consecutive purine bases on one strand of the selected double stranded DNA sequence.

Alternatively, where a mixed sequence comprises a one or more polypurine sequences which include up to about 50% pyrimidine bases on one strand of the double stranded nucleic acid sequence, both purine and pyrimidine bases of the sequence may be read. The pyrimidine bases are read using the following modified purine bases. Cytosine in the polypurine sequence is read by 8-fluoro G, 8-methoxy G, 8-aza G and thymine or uracil is read by 8-fluoro A 8-methoxy A or 8-aza A. Thus, the Oligomer is able to read the interrupting pyrimidine bases of the polypurine sequence so that the Third Strand Oligomer need read only one stonly one strand of the double-stranded nucleic acid sequence. Moreover, modifications to the Third Strand Oligomer to allow it to read both strands of the duplex such as lengthening links, are not needed.

(C) Third Strand Oligomers

Preferred are Oligomers having at least about 7 nucleosides, which is usually a sufficient number to allow for specific binding to a desired purine sequence of a segment of double stranded nucleic acid. More preferred are Oligomers having from about 8 to about 40 nucleotides; especially preferred are Oligomers having from about 10 to about 25 nucleosides. Due to a combination of ease of synthesis, with specificity for a selected sequence, coupled with minimization of intra-Oligomer, internucleoside interactions such as folding and coiling, it is believed that Oligomers having from about 14 to about 18 nucleosides comprise a particularly preferred group.

(1) Preferred Oligomers

These Oligomers may comprise either ribosyl moieties or deoxyribosyl moieties or modifications thereof, such as 2'-O-alkyl ribosyl moieties.

Although nucleotide Oligomers (i.e., having the phosphodiester internucleoside linkages present in natural nucleotide Oligomers, as well as other oligonucleotide analogs) may be used according to the present invention, the use of Oligomers having other internucleosidyl linkages such as Oligomers which comprise oligonucleoside alkyl and arylphosphonate analogs, phosphorothioate oligonucleoside analogs, phosphoroamidate analogs and neutral phosphate ester oligonucleotide analogs. However, especially preferred are oligonucleoside alkyl- and aryl-phosphonate analogs in which phosphonate linkages replace one or more of the phosphodiester linkages which connect two nucleosidyl units are included, as well as Oligomers having nonphosphorus linkages. The preparation of some such oligonucleosidyl alkyl and arylphosphonate analogs and their use to inhibit expression of preselected single stranded nucleic acid sequences is disclosed in U.S. Pat. Nos. 4,469,863; 4,511,713; 4,757,055; 4,507,433; and 4,591,614, the disclosures of which are incorporated herein by reference. One particularly preferred class of these phosphonate analogs are methylphosphonate Oligomers.

Synthetic methods for methylphosphate Oligomers ("MP-Oligomers") are described in Lee, B. L. et al. *Biochemistry* 27:3197–3203 (1988) and Miller, P. S., et al., *Biochemistry* 25:5092–5097 (1986), the disclosures of which are incorporated herein by reference.

Oligonucleosidyl alkyl- and aryl-phosphonate analogs wherein at least one of the phosphodiester internucleoside linkages is replaced by a 3'- 5' linked internucleoside methylphosphonyl (MP) group (or "methylphosphonate") may be preferred in some instances. The methylphosphonate linkage is isosteric with respect to the phosphate groups of oligonucleotides. Thus, these methylphosphonate Oligomers ("MP-oligomers") should present minimal steric restrictions to interaction with the selected DNA sequences. Also suitable are other alkyl or aryl phosphonate linkages wherein such alkyl or aryl groups do not sterically hinder the phosphonate linkage or interact with each other. These MP-Oligomers should be more resistant to hydrolysis by various nuclease and esterase activities, since the methylphosphonyl group is not found in naturally occurring nucleic acid molecules. Due to the nonionic nature of the methylphosphonate linkage, these MP-oligomers should be better able to cross cell membranes and thus be taken up by cells. It has been found that certain MP-Oligomers are more resistant to nucleasehydrolysis, are taken up in intact form by mammalian cells in culture and can exert specific inhibitory effects on cellular DNA and protein synthesis (See, e.g., U.S. Pat. No. 4,469,863).

Preferred are MP-Oligomers having at least about seven nucleosidyl units, more preferably at least about 8, which is usually sufficient to allow for specific recognition of the desired segment of double stranded DNA. More preferred are MP-Oligomers having from about 8 to about 40 nucleosides, especially preferred are those having from about 10 to about 25 nucleosides. Due to a combination of ease of preparation, with specificity for a selected sequence and minimization of intra-Oligomer, inter-nucleoside interactions such as folding and coiling, particularly preferred are MP-Oligomers of from about 14 to 18 nucleosides.

Especially preferred are MP-Oligomers where the 5'-internucleosidyl linkage is a phosphodiester linkage and the remainder of the internucleosidyl linkages are methylphosphonyl linkages. Having a phosphodiester linkage on the 5'-end of the MP-Oligomer permits kinase labelling and electrophoresis of the Oligomer and also improves its solubility.

The selected double stranded nucleic acid sequences are sequenced and MP-Oligomers complementary to the purine sequence are prepared by the methods disclosed in the above noted patents and disclosed herein.

As noted above, preferred Oligomers include those comprising nucleosidyl units having purine bases modified to favor the syn conformation. These bases include those modified at the 8-position such as 8-oxo-A, 8-oxo-G, 8-fluoro-A, 8-fluoro-G, 8-methoxy-A, 8-methoxy-G, 8-aza-A 8-aza-G, and other similarly modified purines known in the art.

These Oligomers are useful in determining the presence or absence of a selected double stranded nucleic acid sequence in a mixture of nucleic acids or in samples including isolated cells, tissue samples or bodily fluids.

These Oligomers are useful as hybridization assay probes and may be used in detection assays. When used as probes, these Oligomers may also be used in diagnostic kits.

If desired, labeling groups such as psoralen, chemiluminescent groups, cross-linking agents, intercalating agents such as acridine, or groups capable of cleaving the targeted portion of the viral nucleic acid such as molecular scissors like o-phenanthrolinecopper or EDTA-iron may be incorporated in the MP-Oligomers.

These Oligomers may be labelled by any of several well known methods. Useful labels include radioisotopes as well as nonradioactive reporting groups. Isotopic labels include $^3H$, $^{35}S$, $^{32}P$, $^{125}I$, Cobalt and $^{14}C$. Most methods of isotopic labelling involve the use of enzymes and include the known methods of nick translation, end labelling, second strand synthesis, and reverse transcription. When using radiolabelled probes, hybridization can be detected by autoradiography, scintillation counting, or gamma counting. The detection method selected will depend upon the hybridization conditions and the particular radioisotope used for labelling.

Non-isotopic materials can also be used for labelling, and may be introduced by the incorporation of modified nucleosides or nucleoside analogs through the use of enzymes or by chemical modification of the Oligomer, for example, by the use of non-nucleotide linker groups. Non-isotopic labels include fluorescent molecules, chemiluminescent molecules, enzymes, cofactors, enzyme substrates, haptens or other ligands. One preferred labelling method includes incorporation of acridinium esters.

Such labelled Oligomers are particularly suited as hybridization assay probes and for use in hybridization assays.

When used to prevent function or expression of a double stranded nucleic acid sequence, these Oligomers may be advantageously derivatized or modified to incorporate a nucleic acid modifying group which may be caused to react with said nucleic acid and irreversibly modify its structure, thereby rendering it non-functional. Our co-pending patent application, U.S. Ser. No. 924,234, filed Oct. 28, 1986, the disclosure of which is incorporated herein by reference, teaches the derivatization of Oligomers which comprise oligonucleoside alkyl and arylphosphonates and the use of such derivatized oligonucleoside alkyl and arylphosphonates to render targeted single stranded nucleic acid sequences non-functional.

A wide variety of nucleic acid modifying groups may be used to derivatize these Oligomers. Nucleic acid modifying groups include groups which, after the derivatized Oligomer forms a triple helix structure with the double stranded nucleic acid segment, may be caused to form a covalent linkage, cross-link, alkylate, cleave, degrade, or otherwise inactivate or destroy the nucleic acid segment or a target sequence portion thereof, and thereby irreversibly inhibit the function and or expression of that nucleic segment.

The location of the nucleic acid modifying groups in the Oligomer may be varied and may depend on the particular nucleic acid modifying group employed and the targeted double stranded nucleic acid segment. Accordingly, the nucleic acid modifying group may be positioned at the end of the Oligomer or intermediate the ends. A plurality of nucleic acid modifying groups may be included.

In one preferred aspect, the nucleic acid modifying group is photoreactable (e.g., activated by a particular wavelength, or range of wavelengths of light), so as to cause reaction and, thus, cross-linking between the Oligomer and the double stranded nucleic acid.

Exemplary of nucleic acid modifying groups which may cause cross-linking are the psoralens, such as an aminomethyltrimethyl psoralen group (AMT). The AMT is advantageously photoreactable, and thus must be activated by exposure to particular wavelength light before cross-linking is effectuated. Other cross-linking groups which may or may not be photoreactable may be used to derivatize these Oligomers.

Alternatively, the DNA modifying groups may comprise an alkylating agent group which, on reaction, separates from the Oligomer and is covalently bonded to the DNA segment to render it inactive. Suitable alkylating agent groups are known in the chemical arts and include groups derived from alkyl halides, haloacetamides, phosphotriesters and the like.

DNA modifying groups which may be caused to cleave the DNA segment include transition metal chelating complexes such as ethylene diamine tetraacetate (EDTA) or a derivative thereof. Other groups which may be used to effect cleaving include phenanthroline, porphyrin or bleomycin, and the like. When EDTA is used, iron may be advantageously tethered to the Oligomer to help generate the cleaving radicals. Although EDTA is a preferred DNA cleaving group, other nitrogen containing materials, such as azo compounds or nitreens or other transition metal chelating complexes may be used.

The nucleosidyl units of Third Strand Oligomers which read purine bases on both strands of a double stranded DNA sequence may comprise a mixture of purine and pyrimidine bases or only purine bases.

Where purine bases on both strands of a double stranded DNA sequence are to be read, it is preferred to use Oligomers having only purine bases. It is believed that such purine-only Oligomers are advantageous for several reasons: (a) purines have higher stacking properties than pyrimidines, which would tend to increase stability of the triple helix structure; (b) use of purines only eliminates the need for either protonation of cytosine (so it has an available hydrogen for hydrogen bonding at the N-3 position at neutral pH) or use of a cytosine analog having such an available hydrogen at the position which corresponds to N3 on the pyrimidine ring; and allows use of a universal lengthening link.

The purine bases (and pyrimidine bases as well) are normally in the anti conformation; however, the barrier for a base to roll over to the syn conformation is low. In formation of the third triple helix, the purines on the Third Strand may assume the syn conformation during the hydrogen bonding process. If desired, it is possible to modify the purine so that it is normally in the syn conformation. For example, the purine may be modified at the 8-position with a substitutent such as methyl, bromo, isopropyl or other bulky group so it will assume the syn configuration under normal conditions. Nucleosidyl units comprising such substituted purines would thus normally assume the syn conformation. Accordingly, where a purine base in the syn conformation is indicated, the present invention contemplates the optional incorporation of such 8-substituted purines in place of unsubstituted A or G. Studies with our (Kendrew) models indicate that such substitutions should not affect formation of the triple helix structure.

Use of purine nucleosidyl units in the anti and syn conformations, as appropriate (following the rules for reading the double stranded DNA described herein) allows reading of the purines on both strands of the duplex and formation of a triple helix structure by the purine-only Third Strand with the double stranded DNA.

If a Third Strand Oligomer comprising both pyrimides and purines is used to read purines on both strands of a double stranded DNA, a non-uniform link format is used as described herein to allow the Third Strand to read across from one strand of the duplex to the other.

(2) Oligomers Comprising Cytosine Analogs

In another aspect of the present invention, novel Oligomers are provided which comprise nucleosidyl units wherein cytosine has been replaced by a cytosine analog comprising a heterocycle which has an available hydrogen at the ring position analogous to the 3-N of the cytosine ring and is capable of forming two hydrogen bonds with a guanine base at neutral pH and thus does not require protonation as does cytosine for Hoogstein-type base pairing, or formation of a triplet.

Suitable nucleosidyl units comprise analogs having a six-membered heterocyclic ring which has a hydrogen available for hydrogen bonding at the ring position corresponding to N-3 of cytosine and which is capable of forming two hydrogen bonds with a guanine base at neutral pH and include 2'-deoxy-5,6-dihydro-5-azadeoxycytidine (I), pseudoisocytidine (II), 6-amino-3-($\beta$-D-ribofuranosyl) pyrimidine-2,4-dione (III) and 1-amino-1,2,4-($\beta$-D-deoxyribofuranosyl)triazine-3-[4H]-one (IV), the structures of which are set forth in Table 5. Also included is 5-methyl cytosine.

(3) Oligomers Comprising Purine Analogs

In a further aspect of the present invention, novel Oligomers are provided which comprise nucleosidyl units which comprise a purine base or analog which has been modified at the 8-position to favor the syn conformation.

In particular, these purine analogs include 8-oxo-A which has been demonstrated to form a triplet with a G•C base pair (see Example 4). The purine analog 8-oxo-G may be used to read the A of an A•T base pair.

Certain 8-modified purine analogs may be used to read the pyrimidine base of a (Watson-Crick) base pair. In particular, the 8-fluoro-A may be used to read T and 8-fluoro G may be used to read C. The 8-methoxy and 8-aza analogs of a and G may be used to read T and C respectively.

(D) Preparation of MP-Oligomers

(1) In General

As noted previously, the preparation of methylphosphonate oligomers has been described in U.S. Pat. Nos. 4,469,863; 4,507,433; 4,511,713; 4,591,614 and 4,757,055.

Preferred synthetic methods for methylphosphonate Oligomers are described in Lin, S., et al., Biochemistry 28:1054–1061 (1989); Lee, B. L., et al., Biochemistry 27:3197–3203 (1988) and Miller, P. S., et al., 25:5092–5097 (1986), the disclosures of which are incorporated herein by reference. Oligomers comprising nucleosidyl units which comprise modified sugar moieties having lengthening links (see FIGS. 5 and 6) may be conveniently prepared by these methods.

Oligomers comprising phosphodiester internucleosidyl phosphorus linkages may be synthesized using any of several conventional methods, including automated solid phase chemical synthesis using cyanoethylphosphoroamidite precursors (29).

If desired, the previously-described nucleosidyl units comprising cytosine analogs (see Table 5) may be incorporated into the MP-Oligomer by substituting the appropriate cytidine analog (see Table 5) in the reaction mixture.

(2) Preparation MP-Oligomers Having Lengthening Links in the Phosphorus Backbone (a) 5'-(Ethyleneoxy)-Substituted-Sugar Intermediates MP-Oligomers may be prepared using modified nucleosides where either the bond between the 5'-carbon and the 5'-hydroxyl or the 3'-carbon and the 3'-hydroxyl of the sugar moiety has been substituted with a alkyleneoxy group, such as ethyleneoxy group.

FIG. 5 shows proposed reaction schemes for preparation of intermediates for modified nucleosides having either a 3'-(ethyleneoxy) or 5'-(ethyleneoxy) link. In FIG. 5, B represents a base, Tr and R represent protecting groups, Tr depicting a protecting group such as dimethoxytrityl and R depicting protecting groups such as t-butyldimethyl silyl or tetrahydropyranyl.

If desired, nucleosidyl units having such lengthening links at both the 3'- and 5'-positions of the sugar moiety may be prepared.

(b) 5'-β-Hydroxyethyl-Substituted Sugar Intermediate

In situations where a double stranded DNA sequence which has purine bases on both strands is to be read, it may be preferred to use MP-Oligomers having a slightly lengthened internucleoside link on the phosphorus backbone.

Such MP-Oligomers may be prepared using nucleosides in which the sugar (deoxyribosyl or ribosyl) moiety has been modified to replace the 5'-hydroxy with a β-hydroxyethyl (HO—$CH_2$—$CH_2$—) group synthetic schemes for the preparation of such a 5'-β-hydroxyethyl-substituted nucleosides is depicted in FIG. 6.

FIG. 6 depicts a proposed reaction scheme for a 5'-β-hydroxyethyl-substituted sugar analog. In FIG. 6, DCC denotes dicyclohexylcarbodiimide, DMSO denotes dimethylsulfoxide. B is a base. Suitable protecting groups, R, include t-butyldimethyl silyl and tetrahydropyranyl.

(c) Preparation of MP-Oligomers Having Lengtheneding Internucleoside Links in the Phosphorus Backbone MP-Oligomers incorporating the above-described modified nucleosidyl units are prepared as described above, substituting the modified nucleosidyl unit.

In the preparation of Oligomers Comprising only purine bases, use of nucleosidyl units having the same lenthening links may be employed. However, in the preparation of Oligomers comprising both pyrimidine (or pyrimidine analog) bases and purine bases, a mixture of nucleosidyl units having no lengthening link and lengthening links are used; nucleosidyl units having lengthening links at both the 3'-carbon and the 5'-carbon of the sugar moiety may be advantageous.

(3) Preparation of Derivatized MP-Oligomers

Derivatized Oligomers may be readily prepared by adding the desired DNA modifying groups to the Oligomer. As noted, the number of nucleosidyl units in the Oligomer and the position of the DNA modifying group(s) in the Oligomer may be varied. The DNA modifying group(s) may be positioned in the Oligomer where it will most effectively modify the target sequence of the DNA. Accordingly, the positioning of the DNA modifying group may depend, in large measure, on the DNA segment involved and its key target site or sites, although such optimum position can be readily determined by conventional techniques known to those skilled in the art.

(a) Preparation of Psoralen-Derivatized MP-Oligomers

The derivatization of MP-Oligomers with psoralens, such as 8-methoxypsoralen and 4'-aminomethyltrimethylpsoralen (AMT), is described in Kean, J. M. et al., Biochemistry 7:9113–9121 (1988) and Lee, B. L. et al., Biochemistry 27:3197–3203 (1988), the disclosures of which are incorporated herein by reference.

(b) Preparation of EDTA-Derivatized MP-Oligomers

The derivatization of MP-Oligomers with EDTA is described in Lin, S. B., et al., Biochemistry 28:1054–1061 (1989), the disclosures of which are incorporated herein by reference.

(E) Utility

According to the present invention, a specific segment of double stranded DNA may be detected or recognized using an MP-Oligomer Third Strand which reads the purine bases of the duplex of the double-stranded nucleic acid according to the triplet base pairing guidelines described herein. The MP-Oligomer Third Strand has a sequence selected such that the base of each nucleosidyl unit will form a triplet with a corresponding base pair of the double stranded nucleic acid DNA to give a triple helix structure. Detectably labeled Oligomers may be used as probes for use in hybridization assays, for example, to detect the presence of a particular double-stranded nucleic acid sequence.

The present invention also provides a method of preventing expression or function of a selected sequence in double stranded nucleic acid by use of an MP-Oligomer which reads the nucleic acid sequence and forms a triple helix structure. Formation of the triple helix may prevent expression and/or function by modes such as preventing opening of the duplex for transcription, preventing of binding of effector molecules (such as proteins), etc. Derivatized Oligomers may be used to detect or locate and then irreversibly modify at target site in the nucleic acid duplex by cross-linking (psoralens) or cleaving one or both strands (EDTA). By careful selection of a target site for cleavage, the Oligomer may be used as a molecular scissors to specifically excise a selected nucleic acid sequence.

The Oligomers may be derivatized to incorporate a nucleic acid reacting or modifying group which can be caused to react with the segment or a target sequence thereof to irreversibly modify, degrade or destroy the nucleic acid and thus irreversibly inhibit its functions.

Thus, these Oligomers may be used to irreversibly inactivate or inhibit a particular gene or target sequence of the game in a living cell, allowing selective inactivation or inhibition. These Oligomers could then be used to permanently inactivate, turn off or destroy genes which produced defective or undesired products or if activated caused undesirable effects.

Another aspect of the present invention is directed to a kit for detecting a particular double stranded nucleic acid sequence which comprises a detectably labeled purine MP-Oligomer Third Strand selected to be able sufficiently complementary to the purine sequence to be able to read the sequence and form a triple helix structure.

To assist in understanding the present invention, the following examples are included which describe the results of a series of experiments, including computer simulations. The following examples relating to this invention should not, of course, be construed in specifically limiting the invention and such variations of the invention, now known or later developed, which would be within the purview of one skilled in the art, are considered to fall within the scope of the present invention as hereinafter claimed.

EXAMPLES

Example 1

Computer Simulations of Triple Helix Structures

The primary purpose of these computer simulations was to determine whether nonionic nucleotide analogs with a methylphosphonate ("MP") backbone would bind with greater affinity in comparison with unmodified oligodeoxynucleotides ("ODN") as the Third Strand of the triple-stranded helical DNA through Hoogsteen-type base pairing. Experimental work suggested that ODN binding to duplex DNA and inhibition of transcription could be via triplet formation (8), but no experimental comparison had been made between analogs with MP backbone verses native ODN in formation of the triple-stranded DNA helix. It was previously unknown whether a nonionic analog with MP backbone could be accommodated in the major groove of triple-stranded helical DNA. Furthermore, the conformation of fully solvated triple-stranded helical DNA with native or MP backbone in the Third Strand had not been determined. Site-specific oligonucleotide binding via double and triple stranded DNA complex formation has recently been shown to suppress transcription of human oncogenes in vitro (8, 9). The goal of this example was to use molecular dynamics simulation to investigate nonionic oligonucleotide analogs with MP backbone in triple-stranded helical complexes, and to gain insight into the molecular mechanism(s) involved in this process.

(A) Simulation Methods

Triple-stranded poly(dT$_{10}$)-poly(dA$_{10}$)-poly(dT$_{10}$) [T$_1$AT$_2$] coordinates were obtained from the A-DNA x-ray structure of Arnott and Selsing (10). The same coordinates were used for the starting geometry of poly(dT$_{10}$)-poly(dA$_{10}$)-poly(dT$_{10}$) methylphosphonate [T$_1$AT$_2$MP]. Geometry optimization and partial atomic charge assignments for the dimethyl ester methylphosphonate fragment were calculated by ab initio quantum mechanical methods with QUEST (version 1.1) using 3-21G*, and STOG*, basis sets, respectively (11). The latter basis set was used to maintain uniform charge assignments with those previously calculated for nucleic acids in the AMBER database. The final monopole atomic charge assignments for the MP fragment were made to obtain a neutral net charge for each base, furanose, and MP backbone of the third DNA strand. Alternating R$_{P-}$ and S$_{P-}$ methyl substitution of the backbone phosphoryl oxygens of the T$_2$MP strand was done by stereo computer graphics. The substitution of MP diastereomers was made in this manner to approximate experimental yield, since the synthesis cannot be controlled. Molecular mechanics and molecular dynamics calculations were made with a fully vectorized version of AMBER (version 3.1), using an all-atom force field (12, 13). All calculations were performed on CRAY X-MP/24 and VAX 8600 computers.

The negative charge of the DNA phosphate backbone was rendered neutral by placement of positive counterions within 4A of the phosphorus atoms bisecting the phosphate oxygens; counterions were not placed on the MP-substituted strand. The triple helices and counterions were surrounded by a 10A shell of TIP3P water (14) molecules with periodic boundary conditions. There are 9,283 and 10,824 atoms in the T$_1$AT$_2$ and T$_1$AT$_2$MP systems, respectively. The box dimensions were 101, 686.8 A$^3$ for T$_1$AT$_2$, and 124,321.1 A$_3$ for T$_1$AT$_2$MP. Initially, the DNA and counterion atoms were fully constrained while the surrounding water molecules were energy minimized using an 8.0A nonbonded cutoff until convergence (root mean-square [rms] of the gradient <0.1 kcal/mole/A). The DNA, counterions, and water were subsequently energy minimized without geometric constraints for an additional 1500 cycles, followed by 220 cycles of minimization with SHAKE activated (15). Molecular dynamics using SHAKE at constant temperature and pressure (300K and 1 bar) was carried out without constraints for 40 psec trajectories for each of the two molecular ensembles.

(B) Results of Simulation Studies

The third DNA strand with MP backbone resulted in several changes consistent with enhanced binding of the ODN with the MP backbone in the triple helix. The average hydrogen bond distances and mean atomic fluctuations are consistently smaller in the T$_1$AT$_2$MP triplet (Table 1) The interstrand phosphorus atoms distance was 9.6A (+/−0.91) for A-T$_2$ and 8.3A (+/−0.58) for A-T$_2$P. The reduced interstrand phosphorus atom distance and smaller mean atomic fluctuations between the second and Third Strands are due to decreased interstrand electrostatic repulsion accompanying MP substitution in the backbone.

Both triple helical DNA systems had strand-specific polymorphic conformational behavior during molecular dynamics. There are significant conformational changes in the furanose relative to the starting geometry in both systems (Table 2). In the T$_1$AT$_2$ helix the furanose ring populations of the T$_1$ and T$_2$ strands remained predominantly in an A-DNA conformation (C3' endo) and the largest proportion of the adenine sugars adopted a B-DNA conformation (C2' endo). A notable percentage of the adenine furanose conformations were in an 01' endo conformation in T$_1$AT$_2$ and T$_1$AT$_2$MP. The sugar puckering pattern of the MP substituted helix had a greater proportion of 01' endo and C2' endo conformations in contrast to the unsubstituted helix. Analysis of other conformational parameters support the hybrid conformational nature of these triple helices. The helical twist angle (between T1 and A strands) averaged 39.4 degrees (+\-2.86) for the $T_1AT_2$ structure and is more consistent with a B-DNA conformation (range 36–45). The $T_1AT_2MP$ helical twist angle averages 32.0 degrees (+\-2.19) and is closer to that of A-DNA (range 30–32.7). The average helical repeat singles (between the T1 and A strands) for the entire structure are for 10.2 $T_1AT_2$ and 11.2 degrees for $T_1AT_2MP$. The average intrastrand phosphorus atom distances over the 40 psec trajectory are presented in Table 3. In both helices, the intrastrand phosphorus distances of the $T_1$ strands are most consistent with an A-DNA conformation (7.0 A). The interstrand phosphorus distances of the $T_2MP$ strand are more consistent with a B-DNA conformation, in contrast to values more consistent with A-DNA for the $T_2$ strand.

We analyzed the coordination of counterions and water along the backbone of the DNA to determine the changes accompanying MP substitution. The average coordination distance and atomic fluctuations-of the counterions with phosphorus atoms was 3.8A (+\-0.6) for $T_1AT_2$ and 4.6A (+\-0.9) for the $T_1AT_2MP$ helix. The increase in average coordination distance and atomic motion in $T_1AT_2MP$ (by 0.8A) is most likely due to the proximity of Rp (axial projecting) methyl groups to the counterions coordinated to the second strand. The average number of water molecules coordinated to the phosphate groups is not significantly altered in the MP substituted helix.

The DNA backbone and the C1'-N (base) dihedral transitions of the two helical systems are shown in Table 4. Comparisons of the α-dihedral of the adenine strands reveals a slight change in the average position of the dihedral with MP substitution, positioning the dihedral closer to trans, but there is a large overlap in the transitional motions of both dihedrals during the 40 psec trajectory. There was a significant change (by 27.0 degrees) in the average Sp-MP diastereomer β dihedral angle from baseline. The fluctuation of the β dihedral containing the Sp-MP diastereomer was significantly less than the Rp-MP.

(C) Interpretation of Simulation Results

The results of these molecular dynamics calculations predict that an MP-substituted ODN incorporated as a colinear Third Strand with Hoogsteen pairing will form a more stable triple helical complex than a native ODN as the Third Strand, as in the case of poly(dT)poly(dA)poly(dT). The enhanced binding of the MP strand is due to reduced interstrand electrostatic repulsion. The MP-substituted helix has reduced hydrogen bond distances, decreased interstrand A-$T_2$ phosphorus distances, and less fluctuation in atomic position relative to the native triple helix. The closer fit and reduced atomic motion during molecular dynamics are qualitatively consistent with a greater enthalpy of binding and stability of the MP-substituted triple helical complex. These findings support the MP-substitution of the Third Strand facilitates formation of a more cohesive triple helical structure by decreased interstrand phosphate repulsion, and will secondarily have closer approximation of Hoogsteen and Watson-Crick hydrogen bond interactions. One would expect predominant effects on Hoogsteen pairing, but there is an unexpected enhancement of Watson-Crick hydrogen bonding with MP substitution in these calculations. The latter finding is most likely due to decreased electrostatic repulsion and shielding (by the Third Strand) between the $T_1$ and $T_2MP$ strands.

The conformation of these DNA structures differs from experimental data based on the fiber diagram. The structure of poly(dT)poly(dA)-poly(dT) was determined by x-ray diffraction studies under conditions of 92% humidity, and is a low resolution structure (10). The molecular dynamics simulations are of fully solvated DNA structures under periodic boundary conditions with counterions. DNA in solution is generally believed to predominate in the B-form; A-DNA conformation predominates under conditions of lower humidity (16). Several triple-stranded DNA helical structures have been determined by x-ray diffraction studies and have been uniformly observed in an A-DNA conformation under conditions of low humidity and increased salt concentration (10,17,18). These computer simulations predict that different DNA conformations coexist within the triple helix, that the individual strands of the helices have predominant conformational populations, and that a Hoogsteen-paired, MP-substituted DNA strand is predicted to predominate in the B-form. The large proportion of 01' endo sugars in both triplexes is of interest since this furanose conformation is 0.6 kcal mole higher than C2' endo and C3, endo DNA sugar puckers (16). The DNA dodecamer crystal structure (19) has a notable 01' endo population, and a significant proportion of 01' endo sugar puckers were observed in molecular dynamics simulations of dsDNA by Seibel et al. (20) Both helical structures generally follow the classical observations of purine nucleotides adopting C2' endo geometries and pyrimidines adopting C3' endo geometries.

The large perturbation of the β dihedral and variable conformational fluctuation of the $R_{P-}$ and $S_{P-}$ MP diastereoisomers in the triplet are due to nonbonded and hydrophobic interactions. The Sp-MP groups are in close proximity to thymine methyl groups (in the major groove) on the same DNA strand, and interact by Van der Waals forces, which could locally destabilize the helix by "locking" the thymine to the Sp-MP backbone. There are greater deviations in the β dihedral of the Rp-MP groups, since these groups project out into the solvent water and are positioned farther away from the thymine methyl groups. There is a known relationship between the orientation of the methyl substituent on the phosphorus atom and DNA duplex stability, and a proposed mechanism of reduced stability of Sp-MP diastereomers is due to local steric interactions (21). Our calculations suggest that steric interactions contribute very little toward local helix destabilization, and the predominant mechanism is mediated by non-bonded interactions between the methyl groups of the Sp-MP backbone and thymine on the same strand which locally destabilizes the DNA.

Example 2

Detection of Triple Helix Formantion Using Circular Dichroism Spectroscopy

Circular dichroism spectroscopy studies were performed using Triple Helix Structures formed using a combination following nucleoside oligomers.

I: d(CTCTCTCTCTCTCTCT)
abbreviated d(CT)$_8$
$E^{254} = 9.2 \times 10^4 M^{-1} cm^{-1}$ II: d(AGAGAGAGAGAGAGAG)
abbreviated d(AG)$_8$
$E^{254} = 1.45 \times 10^5 M^{-1} cm^{-1}$ III: d(CpTpCpTpCpTpCpTpCpTpCpTpCpTpCpTp)
abbreviated d(CpT)$_8$
$E^{254} = 8.5 \times 10^4 M^{-1} cm^{-1}$ Circular dichroism (CD) spectra for the triple helix structures made with (a) 2:1 d(CT)$_8$·d(AG)$_8$ and (b) 1:1:1 d(CT)$_8$·(AG)$_8$·d(CpTp)$_8$ were performed using a CD spectropolarimeter in 0.1M phosphate buffer at the indicated pH.

Figure 11:
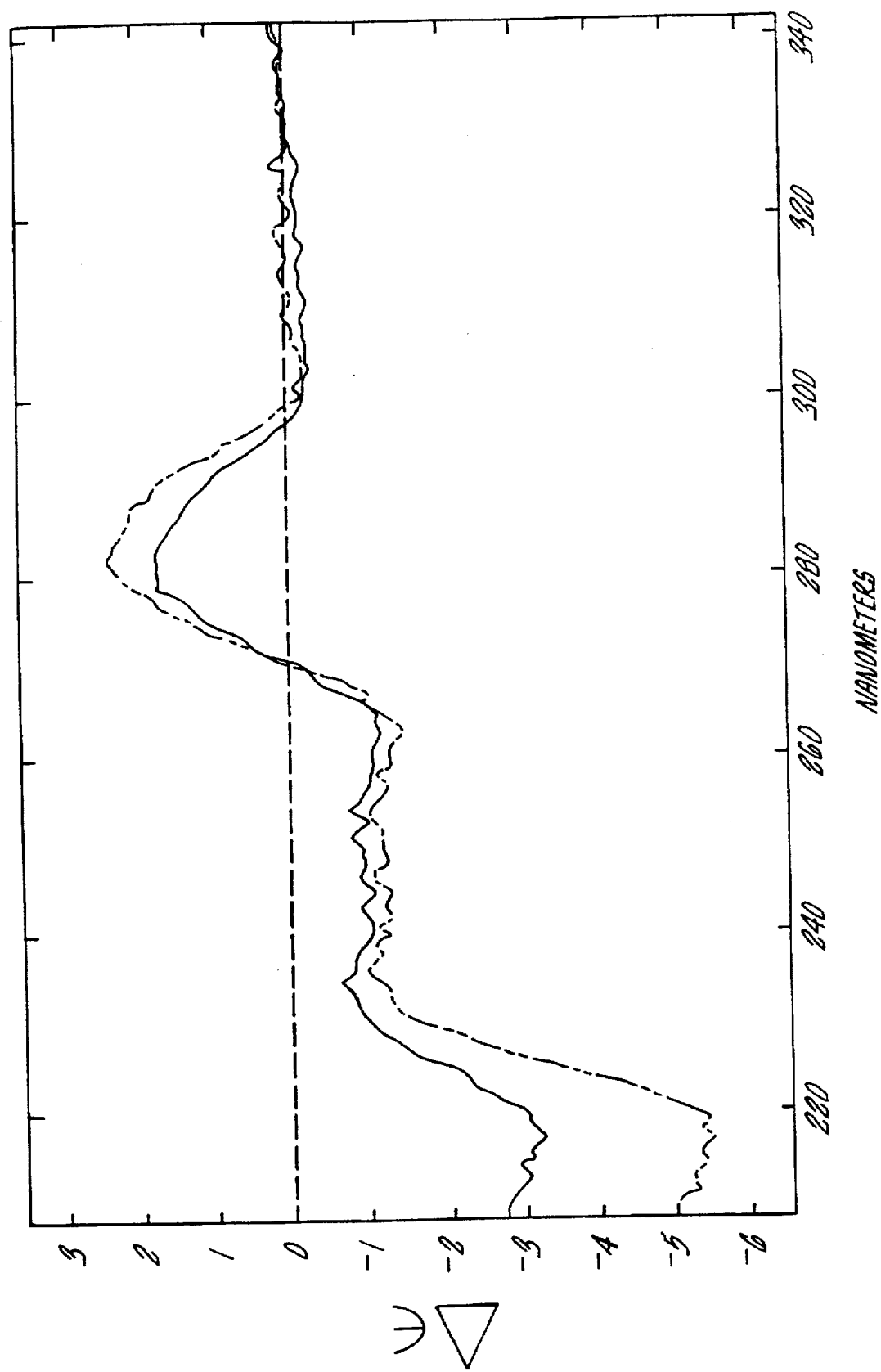
FIG. 11 depicts CD spectra of triple helix structures, (—) depicts a MP-Oligomer Third Strand, (—) depicts an Oligonucleotide Third Strand.

FIG. 11 shows the CD spectra for triple helix (a) [2:1 d(CT)$_8$·d(AG)$_8$] and (b) [1:1:1 d(CT)$_8$·d(AG)$_8$·d(CT)$_8$].

EXAMPLE 3

Crosslinking of Triple Helix Structures Using Psoralen-Derivatized MP-Oligomers Psoralen derivatized dTp(T)$^6$ oligomers were prepared as described in Lee, B. L., et al., Biochemistry 27:3197–3203 (1988).

The T$_7$ oligomers were allowed to hybridize with DNA having the following sequence including a 15-mer poly A subsequence:

```
       5'        10         20         30          40      3'
    d- TAATACGACTCACTATAGGGAGATTTTTTTTTTTTTTACGAGCT
    d- ATTATGCTGAGTGATATCCCTCTAAAAAAAAAAAAAAATGCTCGA
       3'                                              5'
```

MP-oligomers derivatized with 4'-(aminoethyl)aminomethyl-4,5',8-trianethyl-psoralen ["(ae)AMT"], 4'-(aminobutyl)-aminomethyl-4,5',8-trimethylpsoralen ["(ab)AMT"] and 4'-(aminohexyl)aminomethyl-4,5'-8-trimethylpsoralen ["(ah)AMT"] were allowed to hybridize with (a) single stranded DNA of the above DNA sequences and (b) double stranded DNA of the above sequence at 4° C. and were irradiated to cause crosslinking as described in Lee, et al.

Figure 12A:
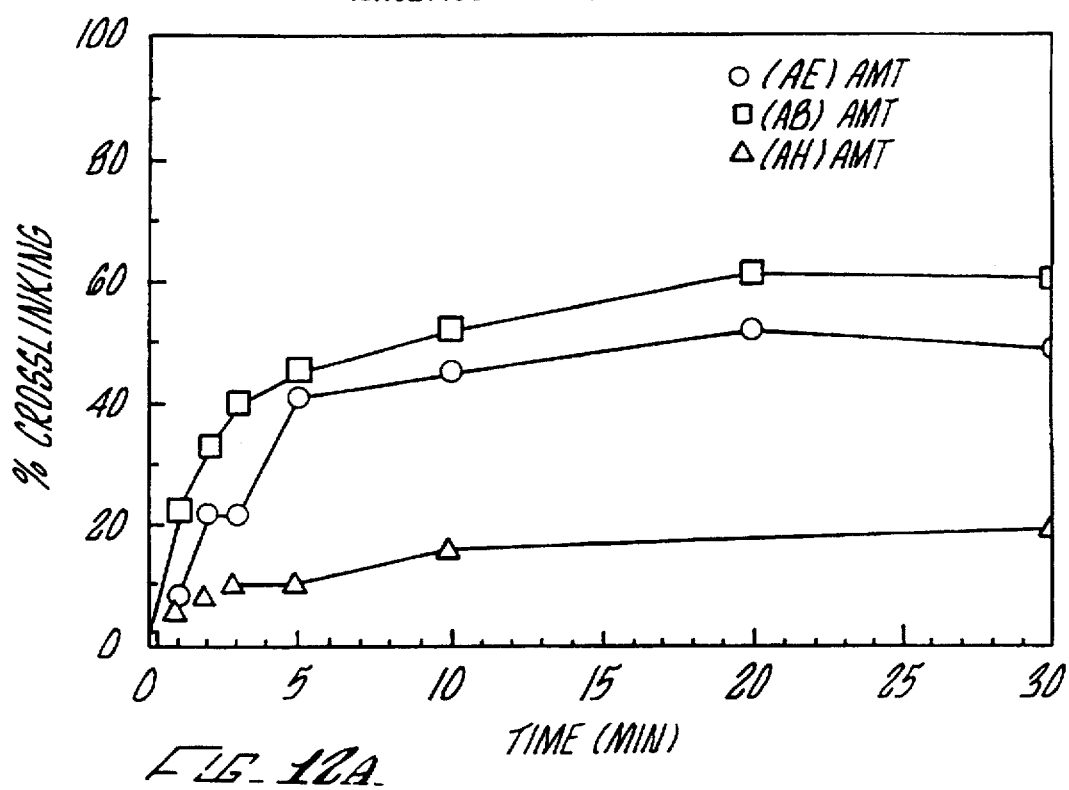
FIG. 12A depicts cross-linking of single stranded DNA using psoralen-derivatized MP-Oligomers.
Figure 12B:
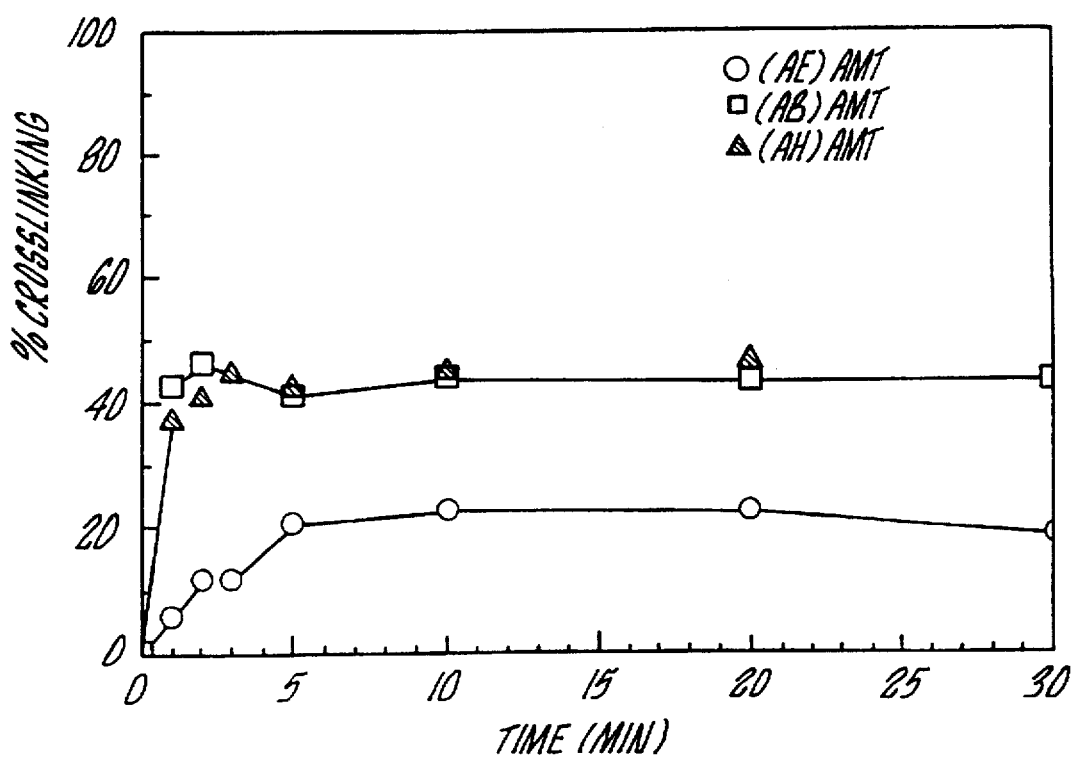
FIG. 12B depicts cross linking of double stranded DNA using psoralen-derivatized MP-Oligomers.

Results are depicted in FIGS. 12A and 12B. FIG. 12A shows crosslinking of the psoralen derivatized T$_7$ Oligomers with the single stranded (poly A containing) DNA sequence.

FIG. 12B shows crosslinking of the double stranded DNA with the double stranded DNA sequence.

Example 4

Formation of Triple Stranded Complexes Using a Third Strand Oligomer

Formation of triple stranded nucleic acid complexes was studied using a Watson-Crick base-paired "target" duplex, II•III, and a Third Strand Oligomer, I, as shown in Table VI. Upon formation of a pyrimidine, purine, pyrimidine triplex, the sugar phosphate base bone of Oligomer I will have the same polarity as purine strand, II, of the duplex.

Figure 13A:
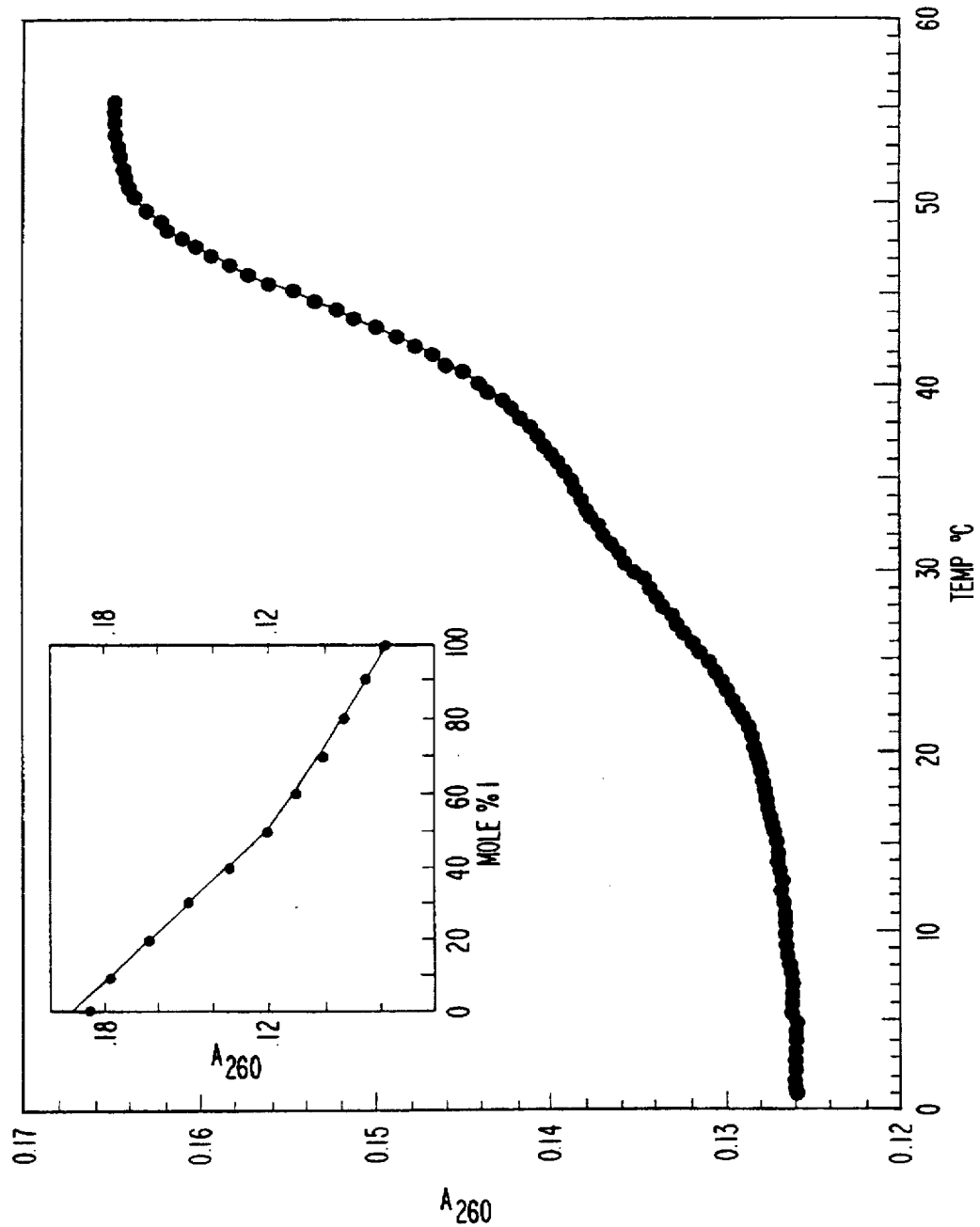
FIG. 13A depicts absorbance versus temperature profile of a solution of 0.5 μM I(OA) and 0.5 μM II•III (G•C). The inset depicts a continuous variation titration of I(OA) and II•III (G•C) at 1.5 μM total strand at 7° C.

At 7° C. mixtures of Oligomer I in which X was 8-oxoadenine, I(OA), and the target duplex in which base pair Y•Z was G•C, II•III (G•C) gave a maximum hypochronicity at 260 nm at a stoichiometry of 1:1 as shown in the inset of FIG. 13A (m-(A). This behavior was consistent with the formation of a triplex, I•II•III (OA•G•C). Upon heating, two coperative transitions were observed. The first, whose midpoint occurred at 29° C. was identified as corresponding to melting of the Third Strand, I(OA. The second, whose midpoint occurred at 45° C. was identified as corresponding to melting of the duplex, II•III (G•C). Similar melting behavior was observed when oligomer I(C) was used. (See Table VI)

Formation of the triplex, I•II•III (OA•G•C) was further confirmed by the circular dichoism (CD) spectra shown in FIG. 13B. At 10° C., the CD spectrum of I(OA)•II•III (G•C) showed DeltaE at 220 nm and 280 nm, behavior which has been identified as characteristic of triplex formation. (See Pilch, D. S., et al., Proc. Natl. Acad. Sci. (USA) 87:1942–1946 (1990)). At 35° C., a temperature above the Tm of the Third Strand, the CD spectrum was essentially identical to the sum of the spectra of I(OA) and II•III (G•C). The CD spectra of the triplex I•II•III (C•G•C) behaved in a similar manner at 10° C. and 40° C., and the spectrum of that triplex was virtually identical to that of I•II•III (OA•G•C).

As shown in FIG. 7, 8-oxoadenosine can form two hydrogen bonds with G (at the N-7 and 0–6 atoms of G). 8-oxo-adenosine has been shown to exist in the keto form with the base in the syn configuration. Triplex formation by I(OA) with II•III (G•C) could occur if the keto form of 8-oxoadenine was in the syn conformation. The proposed hydrogen bonding scheme was supported by the similarities in melting behavior of I•II•III (OA•G•C) and I•II•III (C•G•C) as noted in Table VI.

Examination of molecular models suggested that 8-oxoadenine in the syn configuration could fit at the site opposite the C•G base pair in the triplex (I•II•III (OA•C•G) however, no hydrogen bonding interactions between 8-oxoadenine and C•G would be expected. The melting curve of a 1:1 mixture of I(OA) and II•III (C•G) did show two transitions, although the hyperchronicity of the first transition was only 7% of the total and the melting temperature of the Third Strand was approximately 9° C. A higher melting temperature (13° C. was observed for the Third Strand of triplet (I•II•III (OA•U•A). The increased Tm may be due to formation of a single hydrogen bond between the N-6 exocyclic amino group of 8-oxoadenine and the 0–4 of the uracil in the U•A base pair. Although, a single hydrogen bond could also be formed by 8-oxoadenine and the 0–4 of thymine, no triplex formation was observed for a 1:1 mixture of I(OA) and II•III (T•A). In that instance, triplex formation may be prevented by the interaction of the 5-methyl group of thyamine with the 5-membered ring of 8-oxo-adenine.

Although molecular models suggested that syn-oxoadenine could be accomodated opposite an A•T base pair in the triplex, triplex formation was not observed for a 1:1 mixture of I(OA) and II•III (A•T). This observation may be due to a propensity of the target duplex, II•III (A•T) which contained eleven contiguous A bass to adopt a bent structrure which could disfavor triplex formation. The observation that the Third Strand of I•II•III (T•G•T) melted at 10° C. lower than the Third Strand of I•II•III (C•G•C) supports the above interpretation.

TABLE 1

| AVERAGED HYDROGEN BOND DISTANCES (RMS) | | |
|---|---|---|
| | WITHOUT MP | WITH MP |
| WATSON-CRICK | | |
| ADE HN6B - THY 04 | 2.33 (+/− 0.31) | 1.98 (+/− 0.15) |
| ADE N1 - THY H3 | 2.10 (+/− 0.17) | 1.95 (+/− 0.13) |
| HOOGSTEEN | | |
| ADE HN6A - THY 04 | 2.12 (+/− 0.22) | 2.09 (+/− 0.19) |
| ADE N7 - THY H3 | 1.94 (+/− 0.16) | 1.92 (+/− 0.12) |

Averaged Watson-Crick and Hoogsteen hydrogen bond distances (in Angstroms) in T$_1$AT$_2$ and T$_1$AT$_2$MP helices. These distances are calculated for the triple helical DNA complexes. The fluctuation in atomic position (calculated as the root-mean-square [rms]) are in (Å).

TABLE 2

AVERAGES OF FURANOSE PUCKER (Q), PHASE, AND CONFORMATIONAL POPULATIONS

| HELICAL STRAND | Q MEAN | (RMS) | PHASE | (RMS) | C3'ENDO | O1'ENDO | C2'ENDO | O1' EXO |
|---|---|---|---|---|---|---|---|---|
| A | | | | | | | | |
| T1 | 0.36 | (±0.06) | 35.70 | (±24.7) | 86.8% | 6.6% | 6.6% | 0.0% |
| A | 0.39 | (±0.05) | 107.44 | (±30.8) | 3.6% | 34.3% | 57.1% | 5.0% |
| T2 | 0.38 | (±0.06) | 40.99 | (±24.1) | 75.3% | 24.1% | 0.6% | 0.0% |
| B | | | | | | | | |
| T1 | 0.38 | (±0.06) | 36.31 | (±26.36) | 79.1% | 18.1% | 2.8% | 0.0% |
| A | 0.39 | (±0.05) | 109.78 | (±28.59) | 14.7% | 41.5% | 43.8% | 0.0% |
| T2-MP | 0.40 | (±0.05) | 103.14 | (±29.50) | 11.2% | 61.8% | 27.0% | 0.0% |

Averages of sugar pucker (Q), phase, and conformational populations of furanose for $T_1AT_2$ and $T_1AT_2MP$ helices (15). Q is in Angstroms, phase is in degrees, and populations are in percent of the total furanose conformations in each of the three DNA strands.

TABLE 3

AVERAGE INTRASTRAND PHOSPHATE ATOM DISTANCE (RMS)

| STRAND | WITHOUT MP | WITH MP |
|---|---|---|
| T1 | 6.5 (±/ 0.28) | 6.2 (±/ 0.31) |
| A | 7.0 (±/ 0.26) | 7.1 (±/ 0.24) |
| T2 | 6.3 (±/ 0.29) | 6.8 (±/ 0.26) |

Intrastrand phosphate distances of $T_1AT_2$ and $T_1AT_2MP$ helices. The calculated intrastrand phosphate distances (in Angstroms) averaged over the 40 psec trajectory are shown for the entire triple helical systems. Standard interstrand phosphorus distances are 6.0 Å for A-DNA and 7.0 Å for B-DNA (15).

TABLE 4

| | Without MP | With MP |
|---|---|---|
| α O3' - P - O5' - C5' | | |
| T1 | 280.5 (18.5) | 288.4 (11.3) |
| A | 252.9 (28.7) | 233.2 (28.5) |
| T2 | 285.1 (11.6) | 288.5 (11.3) |
| β P - O5' - C5' - C4' | | |
| T1 | 161.2 (11.5) | 168.7 (8.7) |
| A | 151.5 (10.7) | 159.3 (21.5) |
| T2 | 140.8 (8.8) | POR 158.8 (21.9) |
| | | POS 167.8 (8.7) |
| γ O5' - C5' - C4' - C3 | | |
| T1 | 70.6 (14.6) | 62.6 (9.3) |
| A | 104.8 (27.9) | 112.3 (25.5) |
| T2 | 67.2 (10.5) | 64.0 (10.4) |
| δ C5' - C4' - C3' - O3' | | |
| T1 | 90.3 (12.8) | 82.5 (11.1) |
| A | 112.5 (16.7) | 111.6 (17.2) |
| T2 | 88.6 (10.4) | 104.5 (16.5) |
| ε C4' - C3' - O3' - P | | |
| T1 | 196.4 (10.1) | 199.1 (10.6) |
| A | 200.1 (10.9) | 198.0 (13.3) |
| T2 | 197.5 (10.5) | 187.9 (7.8) |
| C3' - O3' - P - O5' | | |
| T1 | 290.8 (10.6) | 290.6 (9.6) |
| A | 282.9 (12.0) | 282.0 (18.5) |

TABLE 4-continued

| | Without MP | With MP |
|---|---|---|
| T2 | 285.0 (10.5) | 280.5 (11.4) |
| PUR O1' - C1' - N9 - C4 | | |
| ADE | 215.3 (14.7) | 212.1 (14.2) |
| PYR | | |
| T1 | 212.3 (11.0) | 205.9 (10.0) |
| T2 | 206.3 (10.7) | 213.9 (13.2) |

Average backbone dihedral angles (rms) for the triple helical DNA structures during the 40 psec trajectory

TABLE 5

CYTIDINE ANALOGS

| Structure | Reference (Preparation) |
|---|---|
| 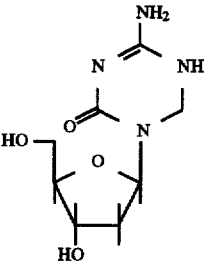 I | Goddard, A.J., et al., Tetrahedron Letters 29:1767 (1988); Beisler, et al., J. Med. Chem. 20:806 (1977) |
| 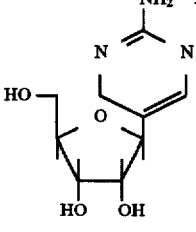 II | Doboszawske, B., et al., J. Org. Chem 53:2777 (1988); Woodcock, T.M., et al., Cancer Res. 40:4234 (1980); Burchenal, J.H., et al., Cancer Res. 36:1520 (1976) |

TABLE 5-continued

CYTIDINE ANALOGS

| Structure | Reference (Preparation) |
|---|---|
| III (NH₂ pyrimidinone nucleoside structure) | Winkley, M.W., et al., J. Chem. Soc. (c), p. 791 (1969) |
| IV (N-amino triazine nucleoside structure) | From 1,2,4-triazine-3(4H)-one (by reaction with ammonium chloride or by (a) nitrosating followed by (b) treatment with sodium borohydride) |

TABLE VI

MELTING TEMPERATURES OF OLIGODEOXYRIBONUCLEOTIDE COMPLEXES

Third Strand[a]: d-C+T.T.C+T.T.T.T.T.T.XT.T.TT (I)
Target Duplex: d.GAA.GAA.AAA.AYA.AAA (II)
CTT.CTT.TTT.TZT.TTT-d (III)

| Complex | | | Tm[b] | |
|---|---|---|---|---|
| X | Y | Z | [c] | [d] |
| 8-oxo A | G | C | 29 | 45 |
| 8-oxo A | C | G | 9 | 41 |
| 8-oxo A | U | A | 13 | 42 |
| 8-oxo A | T | A | — | 44 |
| 8-oxo A | A | T | — | 44 |
| C | G | C | 32 | 45 |
| A | G | C | — | 45 |
| T | A | T | 22 | 48 |

[a]C+ is 5-methyldeoxycytidine
[b]The melting experiments were carried out at an oligomer concentration of 0.5 µM NaCl, 20 mM Mg Cl₂ and 50 mM Tris.HCl, pH 7.0
[c]Transition: triplex -> duplex + 1
[d]Transition: duplex -> single strands

BIBLIOGRAPHY

1. Mosler, H. E., et al., Science 238:645–650 (1987)
2. Povsiz, T. J., et al., J. Am. Chem. Soc. 111:3059–3061 (1989)
3. Wells, R. D., et al., FASEB J. 2:2939–2949 (1988)
4. Dervan, P., Science 232:464–471 (1988)
5. Miller, P. S., et al., Anti-Cancer Drug Design, 2:117–128 (1987)
6. Yarchoan, et al , "AIDS Therapies," Scientific American, pp. 110–119 (October 1988)
7. Sarin, et al., Proc. Nat. Acad. Sci. (USA) 85:7448–7451 (1988)
8. Cooney, M., et al., Science 241:456–459 (1988)
9. Wickstrom, E., et al., Proc. Nat. Acad. Sci. (USA) 85:1028–1032 (1988).
10. Arnoff, S., et al., J. Mol. Biol. 88:509–521 (1974).
11. Singh, U. C., et al., J. Comp. Chem. 5:129–145 (1984).
12. Singh, U. C., et al., AMBER (UCSF) Version 3.1 (1988).
13. Weiner, S. J., et al., J. Comp. Chem. 7:230–252 (1986).
14. Jorgenson, W. J., et al., J. Chem. Phys. 79:926–935 (1983).
15. Berendsen, H. J. C., et al., J. Chem. Phys. 81:3684–3690 (1984).
16. Sanger, W., Principles of Nucleic Acid Structure (Springer-Verlag, New York, 1984)
17. Arnott, S., et al., Nature 244:99–101 (1973)
18. Arnott, S., et al., Science 181:68–69 (1973)
19. Drew, H. R., et al., Proc. Nat. Acad. Sci. (USA) 78:2179–2183 (1981).
20. Seibel, G. L., et al., Proc. Nat. Acad. Sci. (USA) 82:6537–6540 (1985)
21. Bower, M., et al., Nucl. Acids Res. 1:4915–4930 (1987)
22. Donohue, J., et al., J. Mol. Bio. 2:363 (1960)
22a. Ts'o, P.O.P., Basic Principles in Nucleic Acid Chemistry, pp. 453–584 (P.O.P. Ts'o ed., Academic Press, New York, 1974)
23. Sundaralingham, M., Biopolymers 7:821 (1969).
24. Arnott, S., Progr. Nucl. Acid Res. Mol. Biol. 10:183 (1970)
25. Sasisekharan, V., et al., Conform. Biopolym., Pap. Int. Symp. 1967, Vol. 2, p. 641 (1967)
26. Lakshminarayanan, A. V., et al., Biochem. Biophys. Acta 204:49 (1970)
27. Lakshminarayanan, A. V., et al., Biopolymers 8:475 and 489 (1970).
28. Lee, B. L., et al., Nucl. Acids Res. 16:10681–10697 (1988)
29. Barone, A. D., et al., Nucl. Acids. Res. 12:4051–4060 (1984).

We claim:

1. A method of detecting a specific segment of double stranded nucleic acid without interrupting base-pairing of said double stranded nucleic acid which comprises contacting said nucleic acid segment with an Oligomer and detecting said segment, wherein said Oligomer (1) comprises at least one 8-oxo-adenine or 8-oxo guanine nucleosidyl unit, and
(2) is sufficiently complementary to said nucleic acid segment, or a portion of the nucleotide sequences thereof, to form a triple helix structure wherein (a) one strand of the nucleic acid segment comprises a polyhomopurine sequence of at least 7 adjacent purine bases,
(b) the Oligomer is parallel with respect to 5' to 3' orientation to the strand of the nucleic acid segment having the polyhomopurine sequence,
(c) guanine in the polyhomopurine sequence is read by a base in the Oligomer selected from the group consisting of
(i) 8-oxo-adenine, and
(ii) cytosine or a cytosine analog, either of which is protonated at N-3 of cytosine under physiological pH so as to hydrogen bond with guanine, and
(d) adenine in the polyhomopurine sequence is read by a base in the Oligomer selected from the group consisting of 8-oxo-guanine, thymine and uracil.

2. A method according to claim 1, wherein said polyhomopurine sequence comprises at least 12 adjacent purine bases.

3. A method according to claim 1, wherein nucleosides of said Oligomer which comprise 8-oxo-adenine or 8-oxo-guanine are in the syn conformation.

4. A method according to claim 1, wherein nucleosides of the Oligomer which comprise 8-oxoadenine, 8-oxoguanine, 8-fluoroadenine, 8-fluoroguanine, 8-methoxyadenine, 8-methoxyguanine, 8-azaadenine, or 8-azaguanine are in the syn conformation.

5. A method according to claim 1 wherein said Oligomer comprises an oligonucleotide, an alkyl- or aryl-phosphonothioate Oligomer, a phosphorothioate Oligomer, an alkyl- or aryl-phosphonate Oligomer, a phosphotriester Oligomer, a phosphoramidate Oligomer, a carbamate Oligomer, a sulfamate Oligomer, a morpholino Oligomer, or a formacetal Oligomer.

6. A method according to claim 5, wherein nucleosides of said Oligomer comprise sugar moieties selected from ribose, deoxyribose, 2'-O-alkylribose, 2'-O-arylribose, and 2'-halogenribose, all optionally substituted with halogen, alkyl, or aryl.

7. A method according to claim 6, wherein nucleosides of said Oligomer comprise sugar moieties selected from ribose, deoxyribose and 2'-O-methyl ribose.

8. A triple helix structure which comprises a double stranded nucleic acid sequence and an Oligomer which
(1) comprises at least one 8-oxo-adenine or 8-oxo guanine nucleosidyl unit, and
(2) is sufficiently complementary to read a polyhomopurine sequence in one strand of the nucleic acid sequence and to form triplets, wherein
    (a) the Oligomer is parallel with respect to 5' to 3' orientation to the strand having the polyhomopurine sequence,
    (b) guanine in the polyhomopurine sequence is read by a base in the Oligomer selected from the group consisting of
        (i) 8-oxo-adenine, and
        (ii) cytosine or a cytosine analog, either of which is protonated at N-3 of cytosine under physiological pH so as to hydrogen bond with guanine, and
    (c) adenine in the polyhomopurine sequence is read by a base in the Oligomer selected from the group consisting of 8-oxo-guanine, thymine and uracil.

9. A structure according to claim 8, wherein nucleosides of the Oligomer which comprise 8-oxo-adenine or 8-oxo-guanine are in the syn conformation.

10. A structure according to claim 8, wherein nucleosides of the Oligomer which comprise 8-oxo-adenine, 8-oxoguanine, 8-fluoroadenine, 8-fluoro guanine, 8-methoxyadenine, 8-methoxyguanine, 8-azaadenine, or 8-azaguanine are in the syn conformation.

11. A structure according to claim 8 wherein said Oligomer comprises an oligonucleotide, an alkyl- or aryl-phosphonothiate Oligomer, a phosphorothioate Oligomer, a phosphotriester Oligomer, a phosphoramidate Oligomer, a carbamate Oligomer, a sulfamate Oligomer, a morpholino Oligomer, an alkyl- or a formacetal Oligomer.

12. A structure according to claim 8 wherein nucleosides of said Oligomer comprises sugar moieties selected from the group consisting of ribose, deoxyribose, 2'-O-alkylribose, 2'-O-aryl ribose and 2'-halogen ribose, all optionally substituted with halogen, alkyl or aryl.

13. A structure according to claim 12 wherein nucleosides of said Oligomer comprises sugar moieties selected from the group consisting of ribose, deoxyribose and 2'-O-methylribose.

14. A structure according to claim 12 wherein said Oligomer comprises about 12 to about 16 nucleosides.

15. A structure according to claim 8 wherein said Oligomer is an alkyl or aryl phosphonate oligomer.

16. An Oligomer capable of reading a polyhomopurine sequence of one strand of a double stranded nucleic acid sequence, (1) wherein said Oligomer has at least one 8-oxo-adenine nucleosidyl unit,
(2) guanine in the polyhomopurine sequence is read by a base in the Oligomer selected from the group consisting of
    (a) 8-oxo-adenine, and
    (b) cytosine or a cytosine analog, either of which is protonated at N-3 of Cytosine under physiological pH so as to hydrogen bond with guanine, and
(3) adenine in the polyhomopurine sequence is read by a base in the Oligomer selected from the group consisting of 8-oxo-guanine, thymine and uracil.

17. An Oligomer according to claim 16 wherein said Oligomer comprises an oligonucleotide, an alkyl- or aryl-phosphonothiate Oligomer, a phosphotriester Oligomer, a phosphoramidite Oligomer, a carbamate Oligomer, a sulfamate Oligomer, a morpholino Oligomer, or a formacetal Oligomer.

18. An Oligomer according to claim 17 wherein nucleosides of said Oligomer comprises a sugar moiety selected from the group consisting of ribose, deoxyribose, 2'-O-alkyl-ribose, 2'-O-arylribose and 2'-halogen ribose, all optionally substituted with halogen, alkyl or aryl.

19. An Oligomer according to claim 18 wherein nucleosides of said Oligomer comprise a sugar moiety selected from the group consisting of ribose, deoxyribose and 2'-O-methylribose.

20. An Oligomer according to claim 18 which comprises from about 12 to about 16 nucleosides.

21. An Oligomer according to claim 16 which comprises an alkyl- or aryl- phosphonate Oligomer.

22. An Oligomer according to claim 21 which comprises a methylphosphonate Oligomer.

23. A method of making a synthetic Oligomer which binds to a specific segment of double stranded nucleic acid to form a triple helix structure by hydrogen bonding thereto, said method comprising the steps of:
    (a) identifying a double stranded nucleic acid target segment wherein the nucleoside sequence of one strand of the nucleic acid segment comprises a polyhomopurine sequence of at least 7 adjacent purine bases; and
    (b) synthesizing said synthetic Oligomer complementary to said target sequence, said synthetic Oligomer including at least one 8-oxo-adenine or 8-oxo-guanine nucleosidyl unit,
    wherein said synthetic Oligomer has a nucleosidyl unit having a base selected from the group consisting of
        (i) 8-oxo-adenine, and
        (ii) cytosine or a cytosine analog, either of which is protonated at N-3 of cytosine under physiological pH when the complementary location in the polyhomopurine sequence has a G, and
    wherein such synthetic Oligomer has a nucleosidyl unit having a base selected from the group consisting of 8-oxo-guanine, thymine and uracil when the complementary location in the polyhomopurine sequence has an A, and
    wherein said Oligomer is orientated 5' to 3' and binds parallel to the strand having the polyhomopurine sequence.

24. A method according to claim 23 wherein said polyhomopurine sequence comprises at least 12 adjacent purine bases.

25. A method according to claim 23
    wherein said Oligomer has a nucleosidyl unit having a base selected from the group consisting of 8-fluoroguanine, 8-methyoxyguanine and 8-azaguanine when the complementary location in the polyhomopurine sequence has a C, and wherein said Oligomer has a nucleosidyl unit having a base selected from the group consisting of 8-fluoroadenine, 8-methoxyadenine and 8-azaadenine when the complementary location in the polyhomopurine sequence has a T.

26. An Oligomer capable of reading a polyhomopurine sequence of one strand of a double stranded nucleic acid sequence,
(1) wherein said Oligomer has at least one 8-oxo-adenine or 8-oxo-guanine nucleosidyl unit,
(2) guanine in the polyhomopurine sequence is read by a base in the Oligomer selected from the group consisting of
   (a) 8-oxo-adenine, and
   (b) cytosine or a cytosine analog, either of which is protonated at N-3 of cytosine under physiological pH so as to hydrogen bond with guanine,
(3) adenine in the polyhomopurine sequence is read by a base in the Oligomer selected from the group consisting of 8-oxo-guanine, thymine and uracil, and
(4) said Oligomer comprises an alkyl- or arylphosphonate Oligomer.

27. An Oligomer according to claim 26 wherein nucleosidyl units of said Oligomer comprises a sugar moiety selected from the group consisting of ribose, deoxyribose, 2'-O-alkyl-ribose, 2'-O-arylribose and 2'-halogen ribose, all optionally substituted with halogen, alkyl or aryl.

28. An Oligomer according to claim 27 wherein nucleosidyl units of said Oligomer comprise a sugar moiety selected from the group consisting of ribose, deoxyribose and 2'-O-methylribose.

29. An Oligomer according to claim 27 which comprises from about 12 to about 16 nucleosides.

30. An oligomer according to claim 29 which comprises a methylphosphonate Oligomer.

* * * * *